US011299506B2

(12) United States Patent
Peyrottes et al.

(10) Patent No.: US 11,299,506 B2
(45) Date of Patent: Apr. 12, 2022

(54) ACYLNUCLEOSIDE PHOSPHONATES, PRODRUGS THEREOF AND USE THEREOF AS MEDICAMENT

(71) Applicants: UNIVERSITE DE MONTPELLIER, Montpellier (FR); CENTRE NATIONAL DE LA RECHERCHE SCIENTIFIQUE, Paris (FR); ECOLE NATIONALE SUPERIEURE DE CHIMIE DE MONTPELLIER, Montpellier (FR)

(72) Inventors: Suzanne Peyrottes, Grabels (FR); Christian Perigaud, Grabels (FR); Sharon Wein-Grataud, Grabels (FR)

(73) Assignees: UNIVERSITE DE MONTPELLIER, Montpellier (FR); CENTRE NATIONAL DE LA RECHERCHE SCIENTIFIQUE, Paris (FR); ECOLE NATIONALE SUPERIEURE DE CHIMIE DE MONTPELLIER, Montpellier (FR)

( * ) Notice: Subject to any disclaimer, the term of this patent is extended or adjusted under 35 U.S.C. 154(b) by 0 days.

(21) Appl. No.: 16/496,888

(22) PCT Filed: Mar. 21, 2018

(86) PCT No.: PCT/EP2018/057219
§ 371 (c)(1),
(2) Date: Sep. 23, 2019

(87) PCT Pub. No.: WO2018/172435
PCT Pub. Date: Sep. 27, 2018

(65) Prior Publication Data
US 2020/0101091 A1    Apr. 2, 2020

(30) Foreign Application Priority Data
Mar. 23, 2017   (FR) ...................................... 1752405

(51) Int. Cl.
*C07F 9/6561* (2006.01)
*A61P 33/06* (2006.01)
*A61P 33/02* (2006.01)
*A61K 31/52* (2006.01)
*A61K 31/675* (2006.01)
*A61K 31/683* (2006.01)

(52) U.S. Cl.
CPC .......... *C07F 9/65616* (2013.01); *A61K 31/52* (2013.01); *A61K 31/675* (2013.01); *A61K 31/683* (2013.01); *A61P 33/02* (2018.01); *A61P 33/06* (2018.01)

(58) Field of Classification Search
CPC .................................................. C07F 9/65616
See application file for complete search history.

(56) References Cited

U.S. PATENT DOCUMENTS 9,200,020 B2    12/2015 De Jersey et al.

FOREIGN PATENT DOCUMENTS

JP              02096589      *  9/1990

OTHER PUBLICATIONS

Machine translation of JP02096589, published Apr. 9, 1990 (Year: 1990).*
STN record of JP02096589, available online Apr. 9, 1990, accessed Feb. 18, 2021 (Year: 1990).*
Delogu. Mediterranean Journal of Hematology and Infectious Diseases, 2013, 5 (1), 1-8. (Year: 2013).*
Croxen. Nature Reviews: Microbiology, 2010, 8, 26-38 (Year: 2010).*
Castelli. Pharmaceuticals, 2010, 3, 3212-3239 (Year: 2010).*
International Search Report from International Patent Application No. PCT/EP2018/057219, dated Jun. 14, 2018.
Česnek et al., "Synthesis of 9-Phosphonoalkyl and 9-Phosphonoalkoxyalkyl Purines: Evaluation of Their Ability to Act as Inhibitors of Plasmodium falciparum, Plasmodium vivax, and Human Hypoxanthine-guanine-(xanthine) phosphoribosyltransferases", Bioorganic and Medicinal Chemistry (2012), 20(2), pp. 1076-1089.
Dey et al., "Synthesis of tert-Butoxycarbonyl (Boc)-Protected Purines", Journal of Organic Chemistry (2000), 65(22), pp. 7697-7699.
Hazleton et al., "Acyclic Immucillin Phosphonates: Second Generation Inhibitors of Plasmodium falciparum Hypoxanthine-Guanine-Xanthine Phosphoribosyltransferase", Chemical Biology (2012), 19(6), pp. 721-730.
Hocková et al., "Antimalarial Activity of Prodrugs of N-Branched Acyclic Nucleoside Phosphonate Inhibitors of 6-Oxopurine Phosphoribosyltransferases", Bioorganic and Medicinal Chemistry (2015), 23(17), pp. 5502-5510.
Kaiser et al., "Synthesis and Evaluation of Novel Acyclic Nucleoside Phosphonates as Inhibitors of Plasmodium falciparum and Human 6-Oxopurine Phosphoribosyltransferases", ChemMedChem (2012), 10(10) pp. 1707-1723.
Kasthuri et al., "Synthesis of (R)- and (S)β-Hydroxyphosphonate Acyclonucleosides: Structural Analogues of Adefovir (PMEA)", Tetrahedron: Asymmetry (2011), 22(14-15), pp. 1505-1511.
Kasthuri et al., "Synthesis and Study of (R)- and (S)-β-Hydroxyphosphonate Acyclonucleosides as Structural Analogues of (S)-HPMPC (Cidofovir)", New Journal of Chemistry (2014), 38(10), pp. 4736-4742.
Kasthuri, Mahesh, "New Antiviral for the Treatment of the Infections Associated with the Emergent Viruses", Doctoral Thesis (Dec. 2011), pp. 1-211.

(Continued)

Primary Examiner — Noble E Jarrell
(74) Attorney, Agent, or Firm — Greer, Burns & Crain, Ltd

(57) ABSTRACT

Chemical compounds are provided belonging to the group of nucleotide analogues. More specifically, acylnucleoside phosphonate compounds are disclosed and also their method of preparation and their use as medicaments, in particular for the prevention and/or the treatment of diseases caused by infection by an organism that is auxotrophic for purines, such as *Plasmodium falciparum*. Also disclosed are pharmaceutical compositions containing such compounds.

13 Claims, 1 Drawing Sheet

(56) References Cited

OTHER PUBLICATIONS

Keough et al., "Aza-Acyclic Nucleoside Phosphonates Containing a Second Phosphonate Group as Inhibitors of the Human, Plasmodium falciparum and vivax 6-Oxopurine Phosphoribosyltransferases and their Prodrugs as Antimalarial Agents", Journal of Medicinal Chemistry (2015), 58(2), pp. 827-846.

Michel et al., "Synthesis of (-)-neplanocin A with the Highest Overall Yield via an Efficient Mitsunobu Coupling", Tetrahedron (2007), 63(39), pp. 9836-9841.

Porcheddu et al., "A Practical and Efficient Approach to PNA Monomers Compatible with Fmoc-Mediated Solid-Phase Synthesis Protocols", European Journal of Organic Chemistry (2008), 20(34), pp. 5786-5797.

* cited by examiner

ACYLNUCLEOSIDE PHOSPHONATES, PRODRUGS THEREOF AND USE THEREOF AS MEDICAMENT

BACKGROUND

The present invention is in the field of chemical compounds belonging to the group of nucleotide analogues.

The invention relates to acylnucleoside phosphonate compounds and also their method of preparation and their use as medicaments, in particular for the prevention and/or the treatment of diseases caused by infection by an organism that is auxotrophic for purines, such as *Plasmodium falciparum*. The invention also relates to pharmaceutical compositions comprising such compounds.

The therapeutic value of a number of nucleotide analogues, in particular the acylnucleoside phosphonates, abbreviated "ANP," has been described in anti-cancer, antiviral and anti-infectious applications.

The article by Kaiser et al. (Chem. Med. Chem. October; 10(10):1707-23; 2015) describes the activity of ANPs inhibiting the 6-oxopurine PhosphoRibosyl Transferase (PRT) of *P. falciparum*. The ANPs described contain as acyclic part in particular (S)-2-(phosphonomethoxy)propanoic acid or (S)-2-(phosphonoethoxy)propanoic acid, that is to say the chain of atoms linking the nucleic base (or nucleobase) and the phosphonate group comprises a hydrogen atom. The Ki observed for some of these compounds on the activity of human hypoxanthine-guanine PhosphoRibosylTransferase (HGPRT) and hypoxanthine-guanine-xanthine Phospho-RibosylTransferase of *Plasmodium falciparum* (PfHGXPRT) are on the order of the micromole. The lowest concentration inhibiting 50% of the growth of *Plasmodium falciparum* strains is observed for a prodrug form of the compound and is on the order of 20 µM.

Hocková et al. (Chem. Med. Chem. October; 10(10): 1707-23; 2015) describe the activity of ANPs inhibiting the 6-oxopurine PhosphoRibosyl Transferase (PRT) of *P. falciparum*. The described compounds are aza-ANPs, the chain of atoms linking the nucleic base (or nucleobase) and the phosphonate group comprising a nitrogen atom.

The international application WO 2013/166545 also describes the activity of aza-ANPs inhibiting the 6-oxopurine PRT of *P. falciparum*.

Keough et al. (J. Med. Chem, 58, 827-846; 2015) describe the synthesis of ANP compounds comprising an oxopurine base and two phosphonate groups; the chain linking the nucleic base (or nucleobase) and the phosphonate groups comprises a nitrogen atom and an oxygen atom.

The article by Cesnek et al. (2012) relates to 9-phosphonoalkyl and 9-phosphonoalkoxyalkyl purine compounds and to the in vitro evaluation of the activity inhibiting hypoxanthine-guanine-xanthine Phospho-RibosylTransferase of *Plasmodium falciparum* (PfHGXPRT).

The dissertation by Mahesh Kasthuri (Kasthuri, Mahesh. *Nouveaux anti-viraux pour le traitemenet des affections associées aux virus émergents* [New antivirals for the treatment of disorders associated with emergent viruses]. Montpellier: 2011. University of Montpellier 2: PhD dissertation, Molecular Engineering, under the direction of Peyrottes, Suzanne. (Available at http://www.theses.fr/2011MON20085) describes ANPs compounds having the following general formula (Z):

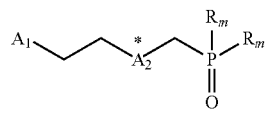

in which:
A₁ represents an adenine or a cytosine,
A₂ represents a —CH₂ group, a —CHOH group, a —CNHN₂ group, a —CN₃ group, a C═O group, a C═N—OH group or a C═N—OBn group,
* indicates that the carbon atom of these different groups is a chiral carbon when A₂ is different a —CH₂ group; and
$R_m$ represents a hydroxyl group, a —ONa group, a —O-methyl group or a —O-ethyl group.

These compounds were found to be inactive as antivirals.

The article by Kasthuri et al. (*Tetrahedron: Assymetry*, 22, 1505-11; 2011) describes the synthesis and the characterization of structural analogues of the antiviral Adefovir (PMEA), used in the treatment of HBV infections. The in vitro tests, in the presence of different viruses, show the absence of antiviral and cytotoxic activity of the compounds.

The article by Kasthuri et al. (*New J. Chem.*, 38, 4736-42, 2014) describes the synthesis and the characterization of structural analogues of the antiviral Cidofovir ((S)-HPMPC), the structure of which comprises a cytosine (pyrimidine). The in vitro tests in the presence of different viruses show the absence of antiviral or cytotoxic activity of the compounds.

Hazelton et al. (*Chem Biol.* 2012 Jun. 22; 19(6):721-30, 2012) describe the activity of compounds belonging to the class of the acyclic immucilline phosphonates, the structure of which is characterized by the presence of a deazapurine base and of a nitrogen atom in the chain of atoms linking said base and the phosphonate group.

Malaria is a major public health problem caused by an infection with parasites of the genus *Plasmodium*, in particular *Plasmodium falciparum* which causes the most severe form of the disease. Due to the appearance of resistance of *P. falciparum* to numerous antimalarial drugs commonly used, such as chloroquine, and, in some regions of the world, artemisinine, it is highly desirable to develop new classes of antimalarials, the mode of action of which is different from that of these medicaments.

SUMMARY

The inventors have designed, synthesized and characterized in vitro ANP compounds including heterocycles, in particular a purine base, and a phosphonate group linked by a chain of atoms —(CH₂)ₙCH₂CH(Y)CH₂—, with n=0, 1 or, said chain being optionally substituted. In an in vitro model of cultured erythrocytes infected with *Plasmodium falciparum*, the inventors have shown that the compounds according to the invention inhibit the growth of the parasite, the 50% growth inhibitory concentration being on the order of the nanomole.

Several compounds according to the invention have a highly significant *Plasmodium falciparum* inhibiting activity while their toxicity for human cells is low, the 50% inhibitory concentration against the growth of human cells being on the order of the millimole. The index of selectivity for

*Plasmodium falciparum* of these compounds is very high (greater than 800); these compounds thus act selectively on this parasite.

Without being bound to a particular theory, among the possible mechanisms of action for the compounds according to the invention, in view of their structure which is analogous to that of the nucleotides, said compounds are capable of targeting the biosynthesis pathway of the purine nucleotides and/or the transporters of purine nucleotides or their precursors. Thus, the therapeutic approach is different from that of the most commonly used antimalarial medicaments, thus addressing the problem posed by the appearance of resistance to these drugs. These compounds therefore represent a very promising approach in the development of medicaments against malaria, and, more generally, due to their mode of action, for the prevention and/or the treatment of diseases caused by an infection by an organism that is auxotrophic for purines, in particular a bacterium or a protozoan.

According to a first aspect, the invention thus relates to the compounds having the following general formula (I):

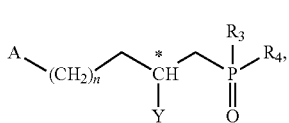
(I)

in which A represents a heterocycle of formula (IIA) or a heterocycle of formula (IIB), as below:

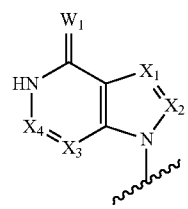
(IIA)

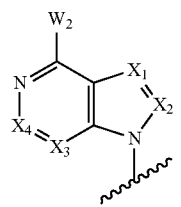
(IIB)

in which:

$W_1$ represents an oxygen atom or a sulfur atom;

$W_2$ represents a halogen atom, a —$OR_5$ group, a —$SR_5$ group, a —$NHR_5$ group or a —$N(R_5)_2$ group;

$X_1$ represents a nitrogen atom or a —CH— group;

$X_2$ represents a nitrogen atom, a —$CR_1$ group or a —C=O group;

$X_3$ represents a nitrogen atom or a —CH— group;

$X_4$ represents a nitrogen atom, a —$CR_2$ group or a —C=O group;

$R_1$ represents:
  a hydrogen atom, or
  a halogen atom, or
  a group selected from:
    a —$NH(R_5)$ group,
    a —$N(R_5)_2$ group,
    a —$OR_5$ group,
    a —$SR_5$ group,
    a $C_1$-$C_6$ alkyl group,
    an aryl group,
    a heteroaryl group;

$R_2$ represents:
  a hydrogen atom, or
  a halogen atom, or
  a group selected from:
    a —$NH(R_5)$ group,
    a —$N(R_5)_2$ group,
    a —$OR_5$ group,
    a $C_1$-$C_6$ alkyl group,
    an aryl group,
    a heteroaryl group;
    a $C_2$-$C_6$ alkenyl group,
    a $C_2$-$C_6$ alkynyl group,
    an aryl($C_1$-$C_6$)alkyl group,
    a ($C_1$-$C_6$)alkylaryl group,
    a heteroaryl($C_1$-$C_6$)alkyl group;

$R_3$ and $R_4$, which are identical or different, each represent, independently of one another:
  a —$OR_6$ group, or
  a —$NHR_7$ group, or
  a —$N(R_7)_2$ group;

$R_5$ represents:
  a hydrogen atom
  a $C_1$-$C_6$ alkyl group,
  a $C_2$-$C_6$ alkenyl group,
  a $C_2$-$C_6$ alkynyl group,
  an aryl group,
  a $C_1$-$C_6$ acyl group,
  an aryl($C_1$-$C_6$)alkyl group,
said groups optionally containing one or more heteroatoms;

$R_6$ represents:
  a hydrogen atom, a sodium atom or a lithium atom, or
  a group selected from an ammonium group or a —$N(R_aR_bR_cR_d)^+$ group with $R_a$, $R_b$, $R_c$ and $R_d$, which are identical or different, each representing a hydrogen atom or a $C_1$-$C_4$ alkyl group, or
  a group selected from:
    an aryl group,
    a S—($C_1$-$C_{12}$)alkyl-2-dithioethyl group, said alkyl group optionally including at least one heteroatom,
    a S—($C_1$-$C_{12}$)aryl-2-dithioethyl group, said aryl group optionally including at least one heteroatom,
    a S—($C_1$-$C_{12}$)acyl-2-thioethyl group, said acyl group optionally including at least one heteroatom,
    a ($C_1$-$C_6$)alkyloxy($C_1$-$C_6$)alkyl ester group,
    an alkoxy($C_1$-$C_6$)carbonyloxymethyl ester group,
    a $C_{12}$-$C_{20}$ alkyl group optionally including at least one heteroatom, $R_7$ represents:
  a $C_1$-$C_6$ alkyl chain, or
  an aryl group, or
  an amino acid residue, an amino acid ester derivative or an amino acid amide derivative;

n is a number equal to 0, 1 or 2;

Y represents a substituent selected from: a halogen atom, a —$OR_5$ group, a —$SR_5$ group, a —$NH(R_5)$ group and a —$N(R_5)_2$ group;

C* represents a chiral carbon atom, the stereoisomers thereof and the pharmaceutically acceptable salts thereof, for their use in the prevention and/or the treatment of an infection by an organism or a microorganism that is auxotrophic for purines, said organism being selected from the bacteria and the protozoans.

According to a second aspect, the invention relates to compounds of formula (I) as such, or to the salts and stereoisomers thereof, with the exception of the compounds of formula (I) in which:
- $W_2$ represents the —$NH_2$ group;
- $X_1$ represents a nitrogen atom;
- $X_2$ represents a —$CR_1$ group in which $R_1$ represents a hydrogen atom;
- $X_3$ represents a nitrogen atom;
- $X_4$ represents a —$CR_2$ group in which $R_2$ represents a hydrogen atom;
- n is equal to 1;
- Y represents a hydroxyl group or an —$NH_2$ group;
- the chiral carbon C* has configuration R or S, and
- $R_3$ and $R_4$ each represent a —$OR_6$ group in which $R_6$ is a sodium atom.

According to a third aspect, the invention relates to the compounds of formula (I) as such, or to the salts and stereoisomers thereof, with the exception of the compounds of formula (I) in which:
- $W_2$ represents the —$NH_2$ group;
- $X_1$ represents a nitrogen atom;
- $X_2$ represents a —$CR_1$ group in which $R_1$ represents a hydrogen atom;
- $X_3$ represents a nitrogen atom;
- $X_4$ represents a —$CR_2$ group in which $R_2$ represents a hydrogen atom;
- n is equal to 1;
- Y represents a hydroxyl group or an —$NH_2$ group;
- the chiral carbon C* has configuration R or S, and
- $R_3$ and $R_4$ each represent a —$OR_6$ group in which $R_6$ is a sodium atom, said compounds being intended to be used as medicament.

Finally, according to a fourth aspect, the invention relates to a pharmaceutical composition including as active ingredient a compound of formula (I), with the exception of the compounds of formula (I) in which:
- $W_2$ represents the —$NH_2$ group;
- $X_1$ represents a nitrogen atom;
- $X_2$ represents a —$CR_1$ group in which $R_1$ represents a hydrogen atom;
- $X_3$ represents a nitrogen atom;
- $X_4$ represents a —$CR_2$ group in which $R_2$ represents a hydrogen atom;
- n is equal to 1;
- Y represents a hydroxyl group or an —$NH_2$ group;
- the chiral carbon C* has configuration R or S, and
- $R_3$ and $R_4$ each represent a —$OR_6$ group in which $R_6$ is a sodium atom, in combination with any pharmaceutically acceptable excipient.

The present invention has, first relates to compounds having the following general formula (I):

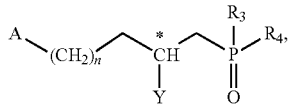

(I)

in which A represents a heterocycle of formula (IIA) or a heterocycle of formula (IIB), as below:

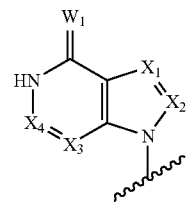

(IIA)

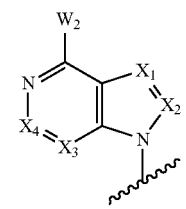

(IIB)

in which:
$W_1$ represents an oxygen atom or a sulfur atom;
$W_2$ represents a halogen atom, a —$OR_5$ group, a —$SR_5$ group, a —$NH(R_5)$ group or a —$N(R_5)_2$ group;
$X_1$ represents a nitrogen atom or a —CH— group;
$X_2$ represents a nitrogen atom, a —$CR_1$ group or a —C=O group;
$X_3$ represents a nitrogen atom or a —CH— group;
$X_4$ represents a nitrogen atom, a —$CR_2$ group or a —C=O group;
$R_1$ represents:
  a hydrogen atom, or
  a halogen atom, or
  a group selected from:
    a —$NH(R_5)$ group,
    a —$N(R_5)_2$ group,
    a —$OR_5$ group,
    a —$SR_5$ group,
    a $C_1$-$C_6$ alkyl group,
    an aryl group,
    a heteroaryl group;
$R_2$ represents:
  a hydrogen atom, or
  a halogen atom, or
  a group selected from:
    a —$NH(R_5)$ group,
    a —$N(R_5)_2$ group,
    a —$OR_5$ group,
    a $C_1$-$C_6$ alkyl group,
    an aryl group,
    a heteroaryl group;
    a $C_2$-$C_6$ alkenyl group,
    a $C_2$-$C_6$ alkynyl group,
    an aryl($C_1$-$C_6$)alkyl group,
    a ($C_1$-$C_6$)alkylaryl group,
    a heteroaryl($C_1$-$C_6$)alkyl group;
$R_3$ and $R_4$, which are identical or different, each represent, independently of one another:
  a —$OR_6$ group, or
  a —$NHR_7$ group, or
  a —$N(R_7)_2$ group;
$R_5$ represents:
  a hydrogen atom
  a $C_1$-$C_6$ alkyl group,
  a $C_2$-$C_6$ alkenyl group, a $C_2$-$C_6$ alkynyl group,
an aryl group,
a $C_1$-$C_6$ acyl group,
an aryl($C_1$-$C_6$)alkyl group,
said groups optionally containing one or more heteroatoms;

$R_6$ represents:
- a hydrogen atom, a sodium atom or a lithium atom, or
- a group selected from an ammonium group or a —N($R_a R_b R_c R_d$)$^+$ group with $R_a$, $R_b$, $R_c$ and $R_d$, which are identical or different, each representing a hydrogen atom or a $C_1$-$C_4$ alkyl group, or
- a group selected from:
  - an aryl group,
  - a S—($C_1$-$C_{12}$)alkyl-2-dithioethyl group, said alkyl group optionally including at least one heteroatom,
  - a S—($C_1$-$C_{12}$)aryl-2-dithioethyl group, said aryl group optionally including at least one heteroatom,
  - a S—($C_1$-$C_6$)acyl-2-thioethyl group, said acyl group optionally including at least one heteroatom,
  - a ($C_1$-$C_6$)alkyloxy($C_1 C_6$)alkyl ester group,
  - an alkoxy($C_1$-$C_6$)carbonyloxymethyl ester group,
  - a $C_{12}$-$C_{20}$ alkyl group optionally including at least one heteroatom, $R_7$ represents:
- a $C_1$-$C_6$ alkyl chain, or
- an aryl group, or
- an amino acid residue, an amino acid ester derivative or an amino acid amide derivative;

n is a number equal to 0, 1 or 2;
Y represents a substituent selected from: a halogen atom, a —OR$_5$ group, a —SRS group, a —NH(R$_5$) group and a —N(R$_5$)$_2$ group;
C* represents a chiral carbon atom,
the stereoisomers thereof and the pharmaceutically acceptable salts thereof, for their use in the prevention and/or the treatment of an infection by an organism or a microorganism that is auxotrophic for purines, said organism being selected from the bacteria and the protozoans.

The definitions below are given according to the present invention.

By convention, in Figures IIA and IIB, the bond between the substituents $X_1$ and $X_2$, on the one hand, and between the substituents $X_3$ and $X_4$, on the other hand, is represented by a double bond in order to represent the most stable form of the compound. However, if $X_2$ and/or $X_4$ represent(s) a —C=O group, the bond between $X_1$ and $X_2$ and/or between $X_3$ and $X_4$ would be represented by a single bond.

"Halogen" is understood to mean a fluorine, chlorine, bromine or iodine atom.

The term "heteroatom" denotes an atom of any known element with the exception of carbon and hydrogen. Preferably, in a compound according to the invention, a heteroatom denotes a nitrogen, oxygen, sulfur or phosphorus atom.

"Hydroxyl group" denotes an —OH group.

The term "ammonium group" denotes the —NH$_4^+$ group. The groups —N(RaRbRcRd)$^+$ can be secondary ammonium groups such as, for example, —NH$_2$(Et)$_2^+$ or —NH$_2$(Et)$_2^+$, tertiary ammonium groups such as, for example, —NH(Et)$_3^+$ or —NH(Me)$_3^+$, or quaternary ammonium groups such as, for example, —N(Bu)$_4^+$.

According to the invention, "$C_1$-$C_{12}$ alkyl group" denotes a monovalent, linear, branched or cyclic hydrocarbon chain comprising 1 to 12 carbon atoms, that is to say comprising 1, 2, 3, 4, 5, 6, 7, 8, 9, 10, 11, 12 carbon atoms. The term "$C_1$-$C_6$ alkyl group" thus denotes an alkyl group comprising 1 to 6 carbon atoms, and "$C_1$-$C_4$ alkyl group" thus denotes an alkyl group comprising 1 to 4 carbon atoms. In a preferred embodiment of the invention, said alkyl group is linear. As examples, one can mention the methyl, ethyl, n-propyl, isopropyl, butyl, n-butyl, isobutyl, tert-butyl, pentyl, isopentyl, hexyl, heptyl, octyl, nonyl, decyl, undecyl and dodecyl or allyl groups.

"$C_{12}$-$C_{20}$ alkyl group" denotes an alkyl group having 12 to 20 carbon atoms, that is to say comprising 12, 13, 14, 15, 16, 17, 18, 19 or 20 carbon atoms. In a compound according to the invention, said carbon chain can include at least one heteroatom and/or one or more double bonds. As examples, one can mention the dodecanyl, tridecanyl, nonadecanyl and eicosanyl groups.

"$C_2$-$C_6$ alkenyl group" is understood to mean a linear, branched or cyclic hydrocarbon chain having 2 to 6 carbon atoms, comprising at least one double bond between two carbon atoms. As examples, one can mention the ethenyl, 1-propenyl, 2-propenyl, 2-methyl-1-propenyl, 1-butenyl and 2-butenyl groups.

"$C_2$-$C_6$ alkynyl group" is understood to mean a linear, branched or cyclic hydrocarbon chain having 2 to 6 carbon atoms, comprising at least one triple bond between two carbon atoms. As examples, one can mention the ethyne, 2-propenyl, 3-butynyl, 2-butynyl, 4-pentynyl, 3-pentynyl, 2-hexylnyl, 3-hexynyl, propargyl and cyanomethyl groups.

"Aryl group" is understood to mean a monocyclic or polycyclic aromatic hydrocarbon group including 5 to 10 carbon atoms. As examples, one can mention the phenyl, naphthyl groups, in particular the 1-naphthyl and 2-naphthyl groups, said groups being possibly substituted by one or more substituents selected from a halogen atom and a group selected from: hydroxyl, —NH$_2$, —NO$_2$, —COOH, —CH$_3$, —CF$_3$, —CHF$_2$, —CH$_2$F, =O, —CN, —SH, —SO$_2$H, ($C_1$-$C_6$)alkyl, ($C_1$-$C_6$)alkenyl, secondary amine, tertiary amine and quaternary amine group.

"Aryl($C_1$-$C_6$) alkyl group" is understood to mean an alkyl radial in which one of the hydrogen atoms bound to a carbon atom, typically a terminal or sp hybrid carbon atom, is replaced by an aryl group. As an example, one can mention the benzyl group (Bn).

"Heteroaryl group" is understood to mean a monocyclic heterocyclic aromatic ring having 5 to 7 chain members or a bicyclic heterocyclic aromatic ring having 7 to 10 chain members, which consists of carbon atoms and of 1 to 4 heteroatoms selected independently from the group consisting of N, O and S, and which is aromatic. As examples, the following can be mentioned: 1H-indazole, dithiazinyl, indolyl, carbazole, quinolizinyl, thiadiazinyl, acridinyl, azocinyl, benzimidazolyl, benzofuranyl, benzothiofuranyl, benzothiophenyl, benzoxazolyl, benzothiazolyl, benzotriazolyl, benztetrazolyl, benzisoxazolyl, benzisothiazolyl, benzimidazalonyl, carbazolyl, β-carbolinyl, chromanyl, chromenyl, cinnolinyl, decahydroquinolinyl, dihydrofuro [2, 3-b] tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinoleinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, quinazolinyl, quinoleinyl, 4H-quinolizinyl, quinoxalinyl, quinuclidinyl, carbolinyl, 6H-1,2,5-thiadiazinyl, 1,2,3-thiadiazolyl, 1,2,4-thiadiazolyl, 1,2,5-thiadiazolyl, 1,3,4-thiadiazolyl, Thianhrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl and xanthenyl. In another aspect of the invention, examples of heteroaryl groups are indolyl, benzimidazolyl, benzofuranyl, benzothiofuranyl, benzoxazolyl, benzothiazolyl, benzotriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl and tetrazolyl, said groups being possibly substituted by one or more substituents selected from: a halogen atom and a group selected from: a hydroxyl, —$NH_2$, —$NO_2$, —COOH, —$CH_3$, —$CF_3$, —$CHF_2$, —$CH_2F$, =O, —CN, —SH, —$SO_2H$, ($C_1$-$C_6$)alkyl, ($C_1$-$C_6$)alkenyl, secondary amine, tertiary amine and quaternary amine group.

"Heteroaryl($C_1$-$C_6$)alkyl group" is understood to mean a heteroaryl group as defined above and bound by a carbon atom or a heteroatom to a $C_1$-$C_6$ alkyl chain as defined above.

"Heterocycle" is understood to mean a ring having five, six or seven ring members, possibly containing one or more heteroatoms selected from N, O or S. The ring can be saturated or unsaturated and can optionally bear one or more substituents selected from: a halogen atom and a group selected from: a hydroxyl group, —$NH_2$, —$NO_2$, —COOH, —$CH_3$, —$CF_3$, —$CHF_2$, —$CH_2F$, =O, —CN, —SH, —$SO_2H$, ($C_1$-$C_6$)alkyl, ($C_1$-$C_6$)alkenyl, secondary amine, tertiary amine and quaternary amine group.

"$C_2$-$C_6$ acyl group" is understood to mean a group including a saturated or unsaturated, linear, branched or cyclic monovalent hydrocarbon chain comprising 2 to 6 carbon atoms. As examples, one can mention the $CH_3CO$— group, the $CH_3CH_2CH_2CO$— group and the $C_6H_5CO$— group.

"S—($C_1$-$C_{12}$)alkyl-2-dithioethyl group" is understood to mean an alkyl group including 1 to 12 carbon atoms, as defined above, substituted by a dithioethyl group.

"Alkyloxy($C_1$-$C_6$)carbonyloxymethyl ester group" is understood to mean an alkyl group including 1 to 6 carbon atoms, as defined above, substituted by an O—CO—O—$CH_2$— group.

"S—($C_1$-$C_{12}$)aryl-2-dithioethyl group" is understood to mean an aryl group as defined above, in particular having 1 to 12 carbon atoms, substituted by an S—S—($CH_2$)$_2$— group.

"S—($C_1$-$C_6$)acyl-2-thioethyl group" or "SATE" is understood to mean an alkyl or aryl group including 1 to 6 carbon atoms, as defined above, substituted by a —CO—S—($CH_2$)$_2$ group; as examples, one can mention S-benzoyl-2-thioethyl.

"($C_1$-$C_6$)acyloxy($C_1$-$C_6$)alkyl ester group" is understood to mean an alkyl or aryl group including 1 to 6 carbon atoms, as defined above, substituted by a —CO—O—$CH_2$— group.

The term "substituted" denotes the replacement of at least one hydrogen, atom by a substituent selected from: a halogen atom and a group selected from: a hydroxyl, —$NH_2$, —$NO_2$, —COOH, —$CH_3$, —$CF_3$, —$CHF_2$, —$CH_2F$, =O, —CN, —SH, —$SO_2H$, ($C_1$-$C_6$)alkyl, ($C_1$-$C_6$)alkenyl, secondary amine, tertiary amine and quaternary amine group.

The term "ester" denotes compounds containing a carboxyl function which has been esterified with a carbon group, and having formula RCOOR' where R and R' each represent, independently of one another, a $C_1$-$C_{12}$, advantageously $C_1$-$C_6$, alkyl group or an aryl group as defined above.

"Amino acid," abbreviated AA, denotes a carboxylic acid also including a functional amine group. In the sense of the present invention, such an amino acid can be a natural or non-natural amino acid. Said amino acid can be of D or L form. As examples, one can mention, histidine, isoleucine, leucine, lysine, methionine, phenylalanine, tryptophan, valine, alanine, arginine, aspartic acid, cysteine, glutamic acid, glutamine, glycine, ornithine, proline, serine, taurine, tyrosine, pyrrolysine and selenocysteine.

"Amino acid residue" is understood to mean the portion of the amino acid which does not participate in the bond with the phosphorus atom of the phosphonate group and which remains free. For example, an arginine residue will be —$NHCH_2COOH$.

"Amino acid ester derivative" is understood to mean an amino acid, the acid function of which has been substituted by a $C_1$-$C_{12}$, advantageously $C_1$-$C_6$, alkyl group or an aryl group as defined above.

"Amino acid amide derivative" denotes a compound formed by an amino acid as defined above, the acid function of which is bound to a nitrogen atom, and corresponding to the formula AACONH2, or to the formula AACONH—($C_1$-$C_6$)alkyl or to the formula AACONH-aryl, or by at least two amino acids (which, in this case, results in peptides).

"Drug" is understood to mean a pharmacologically active compound of formula (I) in which $R_3$ and $R_4$ represent a —$OR_6$ group, with $R_6$ representing a hydrogen atom, a sodium atom, a lithium atom, an ammonium group or a —$N(R_aR_bR_cR_d)^+$ group with $R_a$, $R_b$, $R_c$ and $R_d$, which are identical or different, each representing a hydrogen atom or a $C_1$-$C_4$ alkyl group.

"Prodrug" is understood to mean a pharmacodynamically inert compound of formula (I), which is capable of being transformed in vitro and/or in vivo into a pharmacologically active drug as defined above.

A chiral or asymmetric atom denotes an atom, each substituent of which is of different type. More particularly, in the compounds according to the present invention, the chiral carbon denoted "C*" has four substituents of different type. In addition, when the groups $R_3$ and $R_4$, which are bound to the phosphorus of a compound according to the invention, are different, said phosphorus atom is chiral.

The different isomers of the compounds according to the invention, that is to say the enantiomers, stereoisomers, rotamers, tautomers, diastereoisomers or racemates, are included in the scope of the present invention. Such isomers can be obtained in a substantially pure form, by using a synthesis pathway which makes it possible to control the stereochemistry of the compounds obtained or the chemical splitting and/or by the use of separation methods, such as, for example, chromatography or recrystallization. All these methods are well known to the person skilled in the art.

According to a particular aspect, the compounds of formula (I), for their use according to the invention, include a mixture of stereoisomers of a compound according to the invention. More particularly, the compounds of formula (I), for their use according to the invention, include a mixture of stereoisomers, the carbon C* of which has configuration R or configuration S, respectively. Even more particularly, when the phosphorus of the compound is chiral, the compounds of formula (I), for their use according to the invention, include a mixture of stereoisomers, the carbon C* of which has configuration R or configuration S, respectively, and/or a mixture of the stereoisomers, the phosphorus of which has configuration R or configuration S, respectively. In such a mixture, for each of the chiral atoms, the respective proportions of the stereoisomers are preferably between 1/99 and 99/1.

According to a more particular aspect, the compounds of formula (I), for their use according to the invention, include a racemic mixture of the stereoisomers of a compound according to the invention. More particularly, the compounds of formula (I), for their use according to the invention, include a racemic mixture of the stereoisomers, the carbon C* of which has configuration R or configuration S, respectively. When the phosphorus of the compound is chiral, the compounds of formula (I), for their use according to the invention, include a racemic mixture of the stereoisomers, the carbon C* of which has configuration R or configuration S, respectively, and/or a racemic mixture of the stereoisomers, the phosphorus of which has configuration R or configuration S, respectively.

According to an even more particular aspect, when the phosphorus of the compound is chiral, the compounds of formula (I), for their use according to the invention, include a mixture of the stereoisomers, the carbon C* of which has configuration R or configuration S, respectively, and the phosphorus of which has configuration R or configuration S, respectively.

According to another particular aspect of the invention, the compounds of formula (I), for their use according to the invention, include the pure enantiomer of the compound, in which the carbon C* has configuration R. According to a particular aspect of the invention, the compounds of formula (I), for their use according to the invention, include the pure enantiomer of the compound, in which the carbon C* has configuration S.

The compounds of the present invention can be obtained by conventional methods well known in the prior art, in particular by a synthesis method controlling the stereochemistry of said carbon C*, thus making it possible to obtain a pure enantiomer or a mixture enriched with one of the enantiomers, relative to the carbon C*. According to an even more particular aspect, for each compound according to the invention, the inventors developed a synthesis method based on the chiral pool making it possible to obtain the pure compound (S), on the one hand, and the pure compound (R), on the other hand.

In addition, according to a particular aspect of the invention, the synthesis pathway used for preparing the compounds according to the invention makes it possible to control the stereochemistry of other possible asymmetric atoms of the compounds, such as, for example, the phosphorus atom of the phosphonate group or one or more carbons of a carbon group of a compound, in particular an amino acid derivative.

The compounds according to the invention can be obtained by synthesis steps which are well known to the person skilled in the art, and from commercially available and inexpensive compounds. The stereochemistry of the final molecules originates from the chirality of the amino acids used for the synthesis (aspartic acid) and is controlled throughout the entire synthesis.

In a particular embodiment of the invention, the compounds, for their use according to the invention, correspond to formula (I) in which:
$W_2$ represents a —O($R_5$) group in which $R_5$ represents a $C_1$-$C_6$ alkyl group, or $W_2$ represents a group represents a —S($R_5$) group in which $R_5$ represents a $C_1$-$C_6$ alkyl group, or $W_2$ represents a group represents a —N($R_5$)$_2$ group in which $R_5$ represents a $C_1$-$C_6$ alkyl group, or $W_2$ represents a group represents a —NH($R_5$) group in which $R_5$ represents a $C_1$-$C_6$ alkyl group, or $W_2$ represents a group represents a —NH$_2$ group.

According to another particular aspect, the compounds, for their use according to the invention, correspond to formula (I) in which:
$W_1$ represents an oxygen atom; or $W_2$ represents a —NH($R_5$) group, a —N($R_5$)$_2$ group or a —NH$_2$ group;
$X_1$ represents a nitrogen atom;
$X_2$ represents a —CH group;
$X_3$ represents a nitrogen atom;
$X_4$ represents a —CH group.

According to another particular aspect, the compounds of formula (I), for their use according to the invention, are characterized in that Y represents a —O$R_5$ group, with $R_5$ representing: a hydrogen atom, a $C_1$-$C_6$ alkyl group, a $C_2$-$C_6$ alkenyl group, a $C_2$-$C_6$ alkynyl group, an aryl group, a $C_1$-$C_6$ acyl group, or an aryl($C_1$-$C_6$) alkyl group. According to an even more particular aspect, $R_5$ represents a methyl, ethyl, benzyl, propargyl, allyl or cyanomethyl group.

According to another particular aspect, the compounds of formula (I), for their use according to the invention, have one of the following structural characteristics:
$R_3$ and $R_4$ represent a hydroxyl group;
$R_3$ and $R_4$ represent a —O$R_6$ group in which $R_6$ represents a sodium atom or a lithium atom.

According to another particular aspect, the compounds of formula (I), for their use according to the invention, have one of the following structural characteristics:
$R_3$ represents a —O$R_6$ group, and $R_4$ a —NH$R_7$ group;
$R_3$ represents a —O$R_6$ group, and $R_4$ a —N($R_7$)$_2$ group;
$R_3$ represents a —NH$R_7$ group, and $R_4$ a —NH($R_7$)$_2$ group;
$R_3$ and $R_4$ represent a —NH$R_7$ group.

According to another particular aspect, the invention relates to the compounds of formula (I) in which A represents a purine selected from: guanine, xanthine, hypoxanthine, adenine and 2,6-diaminopurine, for their use according to the invention.

The term "guanine" corresponds to a heterocycle of formula (IIA) in which:
$W_1$ represents an oxygen atom;
$X_1$ represents a nitrogen atom;
$X_2$ represents a —C$R_1$ group, $R_1$ representing a hydrogen atom;
$X_3$ represents a nitrogen atom;
$X_4$ represents a —C$R_2$ group with $R_2$ representing a —NH$_2$ group.

The term "xanthine" corresponds to a heterocycle of formula (IIA) in which:
$W_1$ represents an oxygen atom;
$X_1$ represents a nitrogen atom;
$X_2$ represents a —C$R_1$ group, $R_1$ representing a hydrogen atom;
$X_3$ represents a nitrogen atom;
$X_4$ represents a —C=O group.

The term "hypoxanthine" corresponds to a heterocycle of formula (IIA) in which:
$W_1$ represents an oxygen atom;
$X_1$ represents a nitrogen atom;
$X_2$ represents a —C$R_1$ group, $R_1$ representing a hydrogen atom;
$X_3$ represents a nitrogen atom;

$X_4$ represents a —$CR_2$ group with $R_2$ representing a hydrogen atom.

The term "adenine" corresponds to a heterocycle of formula (IIB) in which:
- $W_2$ represents a —$NH_2$ group;
- $X_1$ represents a nitrogen atom;
- $X_2$ represents a —$CR_1$ group, $R_1$ representing a hydrogen atom;
- $X_3$ represents a nitrogen atom;
- $X_4$ represents a —$CR_2$ group with $R_2$ representing a hydrogen atom.

The term "2,6-diaminopurine" corresponds to a heterocycle of formula (IIB) in which:
- $W_2$ represents a —$NH_2$ group;
- $X_1$ represents a nitrogen atom;
- $X_2$ represents a —$CR_1$ group, $R_1$ representing a hydrogen atom;
- $X_3$ represents a nitrogen atom;
- $X_4$ represents a —$CR_2$ group with $R_2$ representing a —$NH_2$ group.

Among the compounds of formula (I), for their use according to the present invention, mention can be made of the compounds in which A represents a 6-oxopurine selected from guanine, xanthine and hypoxanthine, and more particularly the compounds in which A represents guanine.

Among the compounds of formula (I), for their use according to the present invention, one can also mention the compounds in which A represents a 6-aminopurine selected from adenine and 2,6-diaminopurine, and more particularly the compounds in which A represents 2,6-diaminopurine.

According to a particular aspect, among the compounds of formula (I), for their use according to the present invention, one can mention the compounds in which n is equal to 0, 1 or 2; the carbon chain between the heterocycles and the phosphonate group then includes 3, 4 or 5 carbon atoms, respectively. More particularly, one can mention the compounds of formula (I) in which n is equal to 1.

More particularly, among the compounds of formula (I), for their use according to the present invention, one can mention the compounds in which A represents guanine, xanthine or hypoxanthine, and more particularly guanine, and n is equal to 0, 1 or 2, and more particularly n is equal to 1.

Among the compounds of formula (I), for their use according to the present invention, one can also mention the compounds in which A represents adenine or 2,6-diaminopurine, and more particularly 2,6-diaminopurine, and n is equal to 0, 1 or 2, and more particularly n is equal to 1.

According to another particular aspect, among the compounds of formula (I), for their use according to the present invention, one can mention the compounds in which Y represents the hydroxyl group. According to another particular aspect, among the compounds of formula (I), for their use according to the present invention, one can mention the compounds in which Y represents a hydrogen atom or a —$NH_2$ group.

More particularly, among the compounds of formula (I), for their use according to the present invention, one can mention the compounds in which A represents guanine, xanthine or hypoxanthine, n is equal to 0, 1 or 2, and Y represents the hydroxyl group.

Among the compounds of formula (I), for their use according to the present invention, one can also mention the compounds in which A represents adenine or 2,6-diaminopurine, n is equal to 0, 1 or 2, and Y represents the hydroxyl group.

More particularly, among the compounds of formula (I), for their use according to the present invention, one can mention the compounds in which A represents guanine or 2,6-diaminopurine, n is equal to 0, 1 or 2, Y represents the hydroxyl group, and $R_3$ and $R_4$ each represent a hydroxyl group.

According to another particular aspect, among the compounds of formula (I), for their use according to the present invention, one can mention the compounds in which $R_3$ and $R_4$ each represent a —$OR_6$ group, and $R_6$ represents a hydrogen atom, a sodium atom, a lithium atom, an ammonium group or a —$N(R_aR_bR_cR_d)^+$ group with $R_a$, $R_b$, $R_c$ and $R_d$, which are identical or different, each representing a hydrogen atom or a $C_1$-$C_4$ alkyl group. Said compounds represent the "drug" form of said compound.

According to another particular aspect, among the compounds of formula (I), for their use according to the present invention, one can mention the compounds in which $R_3$ and $R_4$, which are identical or different, each represent, independently of one another, a —$OR_6$ group, or a —$NHR_7$ group or a —$N(R_7)_2$ group; with $R_6$ representing:
- an aryl group,
- a S—($C_1$-$C_{12}$)alkyl-2-dithioethyl group (or DTE), said alkyl group optionally including at least one heteroatom,
- a S—($C_1$-$C_{12}$)aryl-2-dithioethyl group (or DTE), said aryl group optionally including at least one heteroatom,
- a S—($C_1$-$C_6$)acyl-2-thioethyl group (or SATE), and in particular a S-benzoyl-2-thioethyl group (or PheSATE), said acyl group optionally including at least one heteroatom,
- a ($C_1$-$C_6$)acyloxy($C_1$-$C_6$)alkyl ester group (POM),
- an alkyloxy($C_1$-$C_6$)carbonyloxymethyl ester group (POC) or
- a $C_{12}$-$C_{20}$ alkyl group optionally including at least one heteroatom, in particular an oxygen atom, and $R_7$ represents:
- a $C_1$-$C_6$ alkyl chain,
- an aryl group or an amino acid residue, an amino acid ester derivative or an amino acid amide derivative, said groups represented by $R_6$ or $R_7$ constituting protective groups of the phosphonate functions. The presence of such a protective group is intended to facilitate the passage of the compounds according to the invention through a biological membrane, in particular the membrane of the intestinal epithelium or a cellular membrane, after the in vivo administration and before the entry into the target cell. The nature of such a protective group thus influences the lipophily of the compound and its degradation kinetics.

In particular, among the advantageous compounds of formula (I), for their use according to the present invention, one can mention:
- the compounds of formula (I) characterized in that A represents guanine, n is equal to 1, and Y represents a hydroxyl group,
- the compounds of formula (I) characterized in that A represents 2,6-diaminopurine, n is equal to 1, and Y represents a hydroxyl group.

More particularly, among the advantageous compounds of formula (I), for their use according to the present invention, one can mention the compounds of formula (I) in which A represents guanine, n is equal to 1, Y represents a hydroxyl group, $R_3$ and $R_4$ each represent a —$OR_6$ group, and $R_6$ represents a sodium atom.

Even more particularly, among the advantageous compounds of formula (I), for their use according to the present invention, one can mention:

the compounds of formula (I) in which A represents guanine, n is equal to 1, Y represents a hydroxyl group, the chiral carbon C* has configuration R, $R_3$ and $R_4$ each represent a —$OR_6$ group, and $R_6$ represents a sodium atom;

the compounds of formula (I) in which A represents guanine, n is equal to 1, Y represents a hydroxyl group, the chiral carbon C* has configuration S, $R_3$ and $R_4$ each represent a —$OR_6$ group, and $R_6$ represents a sodium atom.

According to another particular aspect, among the advantageous compounds of formula (I), for their use according to the present invention, one can mention:

the compounds of formula (I) in which A represents guanine, n is equal to 1, Y represents a hydroxyl group, the chiral carbon C* has configuration R, $R_3$ and $R_4$ each represent a —$OR_6$ group, and $R_6$ represents a PheSATE group;

the compounds of formula (I) in which A represents guanine, n is equal to 1, Y represents a hydroxyl group, the chiral carbon C* has configuration S, $R_3$ and $R_4$ each represent a —$OR_6$ group, and $R_6$ represents a PheSATE group.

According to another particular aspect, among the advantageous compounds of formula (I), for their use according to the present invention, one can mention:

the compounds of formula (I) in which A represents 2,6-diaminopurine, n is equal to 1, Y represents a hydroxyl group, the chiral carbon C* has configuration R, $R_3$ and $R_4$ each represent a —$OR_6$ group, and $R_6$ represents a sodium atom;

the compounds of formula (I) in which A represents 2,6-diaminopurine, n is equal to 0, Y represents a hydroxyl group, the chiral carbon C* has configuration R, $R_3$ and $R_4$ each represent a —$OR_6$ group, and $R_6$ represents a sodium atom;

the compounds of formula (I) in which A represents 2,6-diaminopurine, n is equal to 0, Y represents a hydroxyl group, the chiral carbon C* has configuration S, $R_3$ and $R_4$ each represent a —$OR_6$ group, and $R_6$ represents a sodium atom.

In the present invention, "pharmaceutically acceptable" denotes any ingredient which is useful in the preparation of a pharmaceutical composition and which is generally safe, nontoxic, and not undesirable biologically or otherwise, and which is acceptable for veterinary use or for use in humans.

"Pharmaceutically acceptable salts" of a compound denotes salts which are pharmaceutically acceptable, as defined above, and which possess the desired pharmacological activity of the parent compound. Such salts include:

(1) the hydrates and the solvates, (2) the pharmaceutically acceptable acid addition salts, formed with pharmaceutically acceptable inorganic acids such as hydrochloric acid, hydrobromic acid, sulfuric acid, nitric acid, phosphoric acid and similar acids; or formed with pharmaceutically acceptable organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic acid and similar acids, or (3) the pharmaceutically acceptable base addition salts, formed when an acidic proton present in the parent composition is either replaced by a metal ion, for example, an alkali metal ion, an alkaline earth metal ion or an aluminum ion, a sodium ion or a lithium ion, or is coordinated with a pharmaceutically acceptable organic or inorganic base. The acceptable organic bases include diethanolamine, ethanolamine, N-methylglucamine, triethanolamine, tromethamine and the like. The acceptable inorganic bases include the aluminum salts and in particular aluminum hydroxide, calcium hydroxide, potassium hydroxide, sodium carbonate and sodium hydroxide.

In the context of the present invention, "organism that is auxotrophic for purines" is understood to mean a living organism which has no pathway for de novo synthesis of the purine monophosphate nucleosides or which has substantially no such biosynthesis pathway. While the cells of mammals are capable of producing the purine monophosphate nucleosides by de novo synthesis, on the one hand, and by recovery of preformed purine bases, on the other hand, said organisms that are auxotrophic for purines depend on the recovery of the 6-oxopurines originating from the cell host and in particular on the recovery of hypoxanthine. The activity of the enzyme HG(X)PRT (Hypoxanthine-guanine-xanthine phosphoribosyl transferase) is crucial for the replication and the survival of these parasitic organisms; but other enzymes and transporters are also involved in this metabolic recovery pathway. These enzymes and transporters which are indispensable for the survival of the parasite thus constitute potential targets.

The techniques for determining the auxotrophy for purines of an organism are based particularly but not exclusively on the sequencing of the genome of said organism and/or on experiments after gene deletion, these methods being well known to the person skilled in the art.

The compounds according to the invention are particularly indicated for their use for the prevention and/or the treatment of diseases caused by infection by an organism that is auxotrophic for purines. It is known that certain nucleosides can be toxic. The compounds according to the invention present no or substantially no toxicity against mammalian cells.

In the sense of the present invention, said organism that is auzotrophic for purines is a microorganism selected from the bacteria and the protozoans.

According to a particular aspect of the invention, said organism that is auzotrophic for purines is selected from the following:

*Plasmodium* spp., responsible for malaria, in particular *Plasmodium falciparum, Plasmodium vivax, Plasmodium malariae, Plasmodium ovale, Plasmodium knowlesi,*

*Giardia*, in particular *Giardia lamblia,*

*Helicobacter pylori,*

*Mycobacterium tuberculosis,*

*Escherichia coli,*

*Trypanosoma brucei,*

*Babesia*, in particular *Babesia divergens* and *Babesia canis,* and

*Toxoplasma*, in particular *Toxoplasma gondii.*

According to a more particular aspect, the invention relates to a compound according to the invention, for its use in the prevention and/or the treatment of an infection by an agent selected from: *Plasmodium falciparum, Plasmodium vivax, Plasmodium malariae, Plasmodium ovale* or *Plasmodium knowlesi*, and more particularly the prevention and/or treatment of an infection by *Plasmodium falciparum.*

According to an even more particular aspect, the invention relates to a compound according to the invention, for its use in the prevention and/or treatment of malaria which is caused by an infection by *Plasmodium falciparum*. According to a more particular aspect, the invention relates to a compound according to the invention, for its use in the prevention and/or the treatment of uncomplicated malaria, by the oral route, in particular as a treatment of first intent.

According to an even more particular aspect, the invention relates to a compound according to the invention, for its use in the prevention and/or the treatment of a pathology caused by an infection by *Toxoplasma*, in particular *Toxoplasma gondii*.

According to a second aspect, the invention relates to compounds of formula (I), the salts and stereoisomers thereof, with the exception of compounds in which:
- $W_2$ represents the —$NH_2$ group;
- $X_1$ represents a nitrogen atom;
- $X_2$ represents a —$CR_1$ group in which $R_1$ represents a hydrogen atom;
- $X_3$ represents a nitrogen atom;
- $X_4$ represents a —$CR_2$ group in which $R_2$ represents a hydrogen atom;
- n is equal to 1;
- Y represents a group selected from: a hydroxyl group and a —$NH_2$ group;
- the chiral carbon C* has configuration R or S, and
- $R_3$ and $R_4$ are identical and each represent a —$OR_6$ group, and $R_6$ represents a hydrogen atom, a sodium atom, a methyl group or an ethyl group.

According to this second aspect, the invention thus relates to the compounds of formula (I), the salts and stereoisomers thereof, with the exception of compounds in which A represents an adenine and in which n is equal to 1; Y represents a group selected from: a hydroxyl group and a —$NH_2$ group; the chiral carbon C* has configuration R or S, and $R_3$ and $R_4$ are identical and each represent a —$OR_6$ group, and —$R_6$ represents a hydrogen atom, a sodium atom, a methyl group or an ethyl group.

More particularly, the invention relates to compounds of formula (I), characterized in that A represents a 6-oxopurine selected from guanine, xanthine and hypoxanthine, and even more particularly A represents guanine.

Even more particularly, the invention relates to compounds of formula (I), characterized in that A represents a 6-aminopurine selected from adenine and 2,6-diaminopurine, with the exception of compounds in which:
- A represents an adenine,
- n is equal to 1;
- Y represents a group selected from: a hydroxyl group and a —$NH_2$ group;
- the chiral carbon C* has configuration R or S, and
- $R_3$ and $R_4$ are identical and each represent a —$OR_6$ group, and $R_6$ represents a hydrogen atom, a sodium atom, a methyl group or an ethyl group.

More particularly, the invention relates to compounds of formula (I) in which A represents 2,6-diaminopurine.

According to another particular aspect, the invention relates to compounds of formula (I) in which A represents guanine, xanthine, hypoxanthine or 2,6-diaminopurine, and in that:
- n is equal to 1 and/or
- Y represents a hydroxyl group and/or
- $R_3$ and $R_4$ each represent a —$OR_6$ group, and $R_6$ represents a hydrogen atom or a sodium atom or a lithium atom.

Even more particularly, the invention relates to compounds of formula (I) in which A represents guanine, n is a whole number equal to 1, and Y represents a hydroxyl group, and more particularly $R_3$ and $R_4$ each represent a —$OR_6$ group and $R_6$ represents a hydrogen atom, a sodium atom or a lithium atom.

According to another aspect, the invention relates to compounds of formula (I) in which A represents 2,6-diaminopurine, n is a whole number equal to 1, and Y represents a hydroxyl group, and more particularly $R_3$ and $R_4$ each represent a —$OR_6$ group and $R_6$ represents a hydrogen atom, a sodium atom or a lithium atom.

More particularly, the invention relates to compounds of formula (I) in which:
- A represents guanine, n is equal to 1, Y represents a hydroxyl group, the chiral carbon C* has configuration R, and $R_3$ and $R_4$ each represent a —$OR_6$ group, and —$OR_6$ represents a sodium atom;
- A represents guanine, n is equal to 1, Y represents a hydroxyl group, the chiral carbon C* has configuration S, and $R_3$ and $R_4$ each represent a —$OR_6$ group, and $R_6$ represents a sodium atom.

The invention also relates to compounds of formula (I) in which:
- A represents guanine, n is equal to 1, Y represents a hydroxyl group, the chiral carbon C* has configuration R, $R_3$ and $R_4$ each represent a —$OR_6$ group, and —$OR_6$ represents a PheSATE group;
- A represents guanine, n is equal to 1, Y represents a hydroxyl group, the chiral carbon C* has configuration S, $R_3$ and $R_4$ each represent a —$OR_6$ group, and $R_6$ represents a PheSATE group.

The invention also relates to compounds of formula (I) in which:
- A represents 2,6-diaminopurine, n is equal to 1, Y represents a hydroxyl group, the chiral carbon C* has configuration R, and $R_3$ and $R_4$ each represent each represent —$OR_6$ group, and —$OR_6$ represents a sodium atom;
- A represents 2,6-diaminopurine, n is equal to 0, Y represents a hydroxyl group, the chiral carbon C* has configuration S, and $R_3$ and $R_4$ each represent a —$OR_6$ group, and $R_6$ represents a sodium atom;
- A represents guanine, n is equal to 0, Y represents a hydroxyl group, the chiral carbon C* has configuration S, and $R_3$ and $R_4$ each represent a —$OR_6$ group, and $R_6$ represents a sodium atom.

According to a third aspect, the invention relates to compounds of formula (I), the salts and stereoisomers thereof, with the exception of compounds in which:
- $W_2$ represents the group —$NH_2$ group;
- $X_1$ represents a nitrogen atom;
- $X_2$ represents a —$CR_1$ group in which $R_1$ represents a hydrogen atom;
- $X_3$ represents a nitrogen atom;
- $X_4$ represents a —$CR_2$ group in which $R_2$ represents a hydrogen atom;
- n is equal to 1;
- Y represents a group selected from: a hydroxyl group and a —$NH_2$ group;
- the chiral carbon C* has configuration R or S, and
- $R_3$ and $R_4$ are identical and each represent a —$OR_6$ group, and $R_6$ represents a hydrogen atom, a sodium atom, a methyl group or an ethyl group,
- for their use as medicament.

According to a more particular aspect, the present invention relates to compounds of general formula (I) or to the pharmaceutically acceptable salts and stereoisomers thereof, for their use as medicament for the prevention and/or the treatment of an infection by an organism that is auzotrophic for purines and in particular an infection by *Plasmodium* spp.

The invention also relates to compounds according to the invention, which are intended to be used as medicament.

Finally, according to a fourth aspect, the invention relates to a pharmaceutical composition including, as active ingredient, a compound of formula (I), with the exception of compounds in which:

$W_2$ represents the group —$NH_2$ group;

$X_1$ represents a nitrogen atom;

$X_2$ represents a —$CR_1$ group in which $R_1$ represents a hydrogen atom;

$X_3$ represents a nitrogen atom;

$X_4$ represents a —$CR_2$ group in which $R_2$ represents a hydrogen atom;

n is equal to 1;

Y represents a group selected from: a hydroxyl group and a —$NH_2$ group;

the chiral carbon C* has configuration R or S, and $R_3$ and $R_4$ are identical and each represent a —$OR_6$ group, and $R_6$ represents a hydrogen atom, a sodium atom, a methyl group or an ethyl group.

A pharmaceutical composition according to the invention includes at least one compound according to the invention and at least one pharmaceutically acceptable excipient.

"Pharmaceutically acceptable excipient" is understood to mean any substance other than the active ingredient, which is intended to confer a consistency, a flavor, a color to a medicament, while avoiding any interaction with the active ingredient. The pharmaceutically acceptable excipient according to the invention will be selected, depending on the pharmaceutical form and the desired route of administration, from the usual excipients which are known to the person skilled in the art, with a view to being administered to humans or to animals.

The routes of administration, the dosages and the optimal galenic forms of a pharmaceutical composition according to the invention can be determined according to the criteria generally taken into consideration in the determination of a pharmaceutical treatment suited to a subject, such as, for example, the age or the body weight of the patient, the severity of his/her general condition, the tolerance to the treatment, the side effects observed. Depending on the desired administration type, the pharmaceutical composition according to the invention can moreover include at least one pharmaceutically acceptable excipient. The pharmaceutical composition according to the present invention can moreover include at least one pharmaceutical adjuvant known to the person skilled in the art, selected from the thickeners, the preservatives, the perfumes, the dyes, the chemical or mineral filters, the hydration agents, mineral water, etc.

For an anti-malarial treatment, an administration by the oral route is recommended. The appropriate forms of administration will include the forms by the oral route such as tablets, soft or hard gel capsules, powders, granules and oral solutions or suspensions, the sublingual or buccal forms of administration.

According to another particular aspect, the invention also relates to a pharmaceutical composition according to the invention, for its use in the prevention and/or the treatment of a disease caused by an infection by an organism that is auxotrophic for purines, said organism being selected from the bacteria and the protozoans, and in particular malaria caused by an infection by *Plasmodium falciparum*.

According to another particular aspect, the invention also relates to a method for prevention and/or treatment of an infection caused by an organism that is auzotrophic for purines, characterized in that it includes the administration to a subject who has a need for a compound of formula (I).

More particularly, the method for prevention and/or treatment according to the invention is characterized in that said subject is a human or an animal. A method for prevention and/or treatment according to the invention is in particular applicable to a subject suffering from malaria.

Examples 1 and 2 below illustrate the invention.

DETAILED DESCRIPTION

Figures 1A, 1B, 1C:
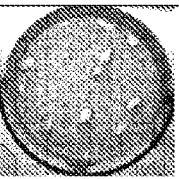
FIGS. 1A to 1C, according to Example 2, show an image representing the experimental results of the detection of the in vitro anti-toxoplasmosis activity of different compounds; compounds No. 3 (FIG. 1A), 5 (FIG. 1B) and 15 (FIG. 1C) are added at the concentrations of 5 (central column) and 50 µM (right column), respectively, to a monolayer of fibroblasts.

Example 1: Synthesis and Chemical Characterization of the Compounds 1.1. General Synthesis Pathway:

The general synthesis pathway is given in diagram 1 for compounds having a purine base.

The exocyclic amine functions of the purine nucleobases (formula I) are protected by protective groups, in particular tert-butoxycarbonyl groups, according to a procedure adapted from the literature (*J. Org. Chem.* 2000, 65, 7697-7699; *Tetrahedron* 2007, 63, 9836-9841; *Eur. J. Org. Chem.* 2008, 5786-5797) in order to obtain precursors (formula II). These precursors are used in a Mitsunobu reaction in the presence of epoxy-alcohols leading to the intermediate products (formula III). The opening of the epoxide by a silylated phosphite diester in the presence of BF3 etherate leads to the desired beta-hydroxyphosphate (formula IV).

The protective groups of the amine functions of the purine nucleobases are eliminated according to the procedures described in the literature leading to compounds of formula V or VI from the compounds of formula IV.

The purine nucleobases are deaminated according to the procedures described in the literature leading to the compounds of formula VII from the compounds of formula VI.

The protective groups of the phosphonate function are eliminated according to the procedures described in the literature leading to the compounds of formula V from the compounds of formula IV and compounds of formula VIII from the compounds of formula VII.

Diagram 1: General synthesis pathway.

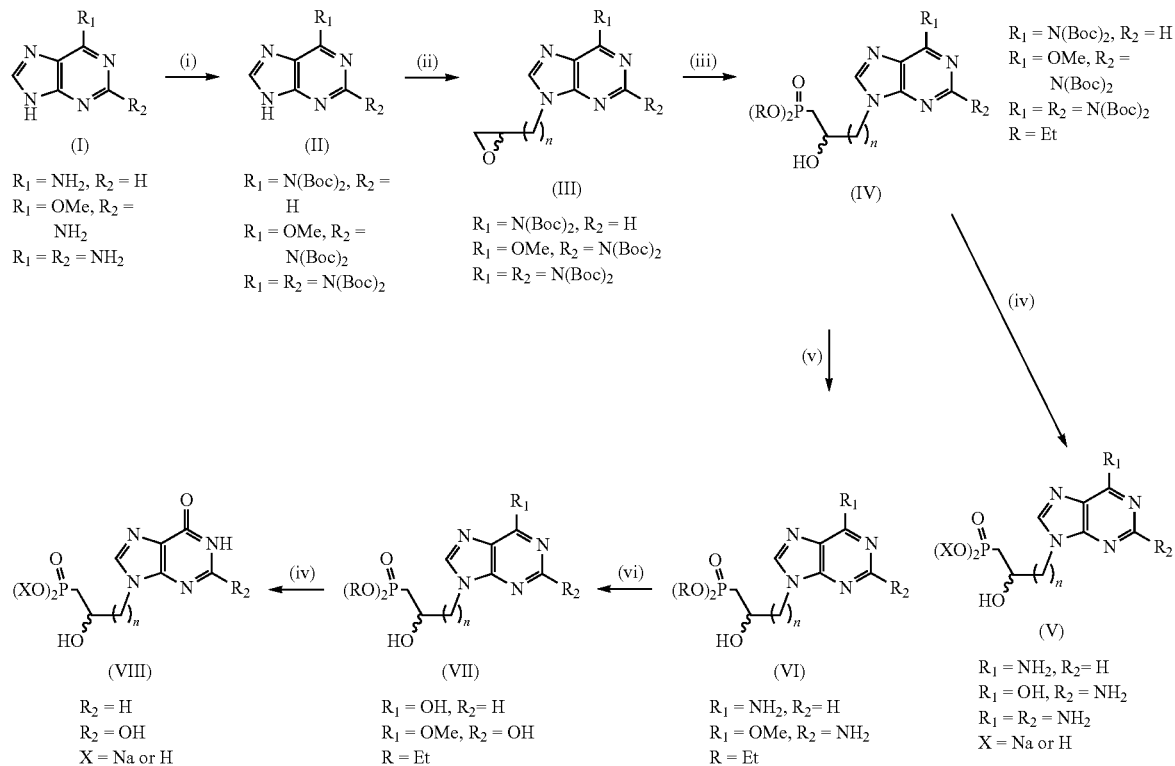

(i) 1) Boc₂O, DMAP, THF, rt, 15 h, 2) NaHCO₃ sat, MeOH, 50° C., 1 h; (ii) (R) or (S)-glycidol (n = 0) or (R) or (S)-(2-hydroxyethyl)oxirane (n = 1), PPh₃, DEAD, THF, rt, 16 h; (iii) 1) HP(O)OEt₂, N,O-BSA, toluene, reflux, 3 h, 2) Compound III, BF₃.OEt₂, CH₂Cl₂, −60° C., 3 h, rt, 16 h; (iv) TMSBr, CH₃CN or DMF, rt, 24 h; (v) TFA, CH₂Cl₂, rt, 5 h; (vi) NaNO₂, H₂O, CH₃COOH, 65° C., 2 h.

1.2. Synthesis of the Compounds of Formula (III)

1.2.1 Synthesis of (R) and (S)-(2-hydroxyethyl)oxirane

These epoxides are prepared in three steps from L- or D-aspartic acid according to a procedure adapted from the literature (*J. Org. Chem.* 1992, 57, 4352-4361) according to the following diagram 2:

Diagram 2. Synthesis of (S)-(2-hydroxyethyl)oxirane.

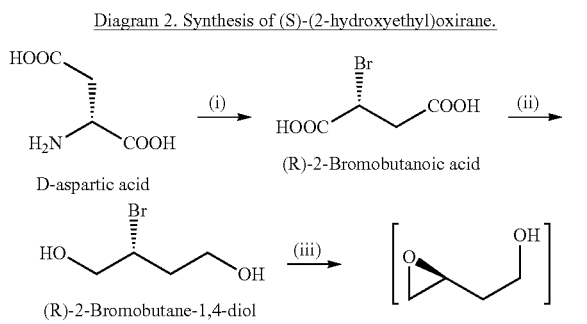

(i) NaNO₂, KBr, H₂SO₄ 2N, 0° C., 3 h; (ii) BH₃•THF, THF, 0° C. to rt, 3 h; (iii) Cs₂CO₃, CH₂Cl₂ rt, 24 h.

1.2.2. Synthesis of the Compounds of Formula (III)

The epoxy-alcohol (for example, (R) or (S)-glycidol or (R) or (S)-(2-hydroxyethyl)oxirane) (1.1 eq.) is added under argon to a solution of compound (II) (1.1 eq.) and of triphenylphosphine (1.2 eq.) in anhydrous THF (1 mL/mmol). The solution is cooled to 0° C., and diethyl-azodicarboxylate (1.2 eq.) is added dropwise. The reaction medium is stirred at temperature under argon overnight. The volatiles are eliminated at reduced pressure, and the residue is taken up in ethyl ether, after one night at 4° C., the solid is eliminated. The filtrate is concentrated and purified on a silica gel column (CH₂Cl₂/MeOH, 0-5% or isocratic AcOEt) leading, after evaporation of the pooled fractions, to the expected compound (formula III).

The following compounds of formula (III) were synthesized:

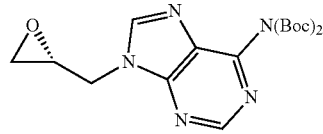

$N^6,N^6$-Bis(tert-butoxycarbonyl)-9-{[(2R)-oxiran-2-yl]methyl} adenine yield=87.7%; colorless oil; $R_f$=0.41 (AcOEt); $[\alpha]^{20}_D$=+22.5 (c 1.02, MeOH);

¹H NMR (CDCl₃): δ=1.46 (s, 18H), 2.52 (dd, 1H, ²J=4.2 Hz, ³J=2.7 Hz), 2.90 (m, 1H), 3.40 (m, 1H), 4.25 (dd, 1H, ²J=15.0 Hz, ³J=6.0 Hz), 4.74 (dd, 1H, ²J=15.0 Hz, ³J=2.7 Hz), 8.16 (s, 1H), 8.87 (s, 1H);

¹³C NMR (CDCl₃: δ=27.9 (6C), 45.4, 45.5, 49.9, 83.9 (2C), 128.6, 145.1, 150.6 (2C), 152.4 (2C), 153.5;

MS (ESI) m/z 392.2 [M+H]+;
HRMS: calc. C₁₈H₂₆N₅O₅ [M+H]+ 392.1934, obs. 392.1921.

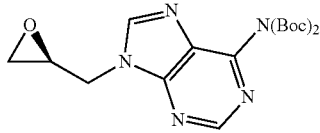

N⁶,N⁶-Bis(tert-butoxycarbonyl)-9{[(2S)-oxiran-2-yl] methyl} adenine yield=86.3%; white solid; R$_f$=0.41 (AcOEt);
[α]²⁰$_D$=−16.8 (c 1.01, MeOH);
¹H NMR (CDCl₃): δ=1.45 (s, 18H), 2.52 (dd, 1H, ²J=4.2 Hz, ³J=2.7 Hz), 2.90 (m, 1H), 3.39 (m, 1H), 4.24 (dd, 1H, ²J=15.0 Hz, ³J=6.0 Hz), 4.73 (dd, 1H, ²J=15.0 Hz, ³J=2.7 Hz), 8.16 (s, 1H), 8.87 (s, 1H);
¹³C NMR (CDCl₃): δ=27.9 (6C), 45.3, 45.5, 49.9, 83.9 (2C), 128.6, 145.1, 150.6 (2C), 152.3 (2C), 153.5;
MS (ESI) m/z 392.3 [M+H]+;
HRMS: calc. C₁₈H₂₆N₅O₅ [M+H]+ 392.1934, obs. 392.1941.

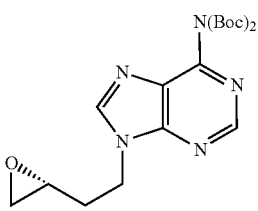

N⁶,N⁶-Bis(tert-butoxycarbonyl)-9{[(2R)-oxiran-2-yl]ethyl}adenine yield=90.7%; colorless oil; R$_f$=0.27 (CH₂Cl₂/MeOH, 95/5, v/v);
¹H NMR (DMSO-d₆): δ=1.37 (s, 18H), 1.99 (m, 1H), 2.20 (m, 1H), 2.32 (m, 1H), 2.58 (m, 1H), 2.97 (m, 1H), 4.46 (t, 2H), 8.66 (s, 1H), 8.83 (s, 1H).

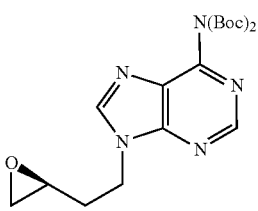

N⁶,N⁶-Bis(tert-butoxycarbonyl)-9{[(2S)-oxiran-2-yl] ethyl}adenine yield=91%; white solid; R$_f$=0.31 (CH₂Cl₂/MeOH, 95/5, v/v);
¹H NMR (DMSO-d₆): δ=1.37 (s, 18H), 2.00 (m, 1H), 2.21 (m, 1H), 2.34 (m, 1H), 2.59 (m, 1H), 2.98 (m, 1H), 4.47 (t, 2H), 8.68 (s, 1H), 8.85 (s, 1H).

¹³C NMR (DMSO-d₆): δ=27.2, 31.9, 39.5, 45.2, 49.2, 83.1, 127.7, 146.8, 148.9, 149.9, 151.2, 153.1.

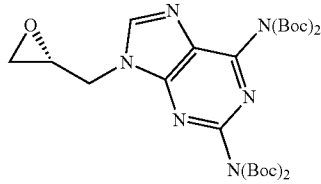

N²,N²—N⁶,N⁶-Tetra(tert-butoxycarbonyl)-9-{[g (2R)-oxiran-2-yl] methyl}2,6-diaminopurine yield=84.8%; white solid; R$_f$=0.55 (AcOEt);
¹H NMR (DMSO-d₆): δ=1.36 (s, 36H), 2.44 (dd, 1H, 2J=4.8 Hz, 3J=2.4 Hz), 2.83 (m, 1H), 3.45 (m, 1H), 4.40 (dd, 1H, 2J=18.0 Hz, 3J=5.7 Hz), 4.67 (dd, 1H, 2J=15.0 Hz, 3J=3.3 Hz), 8.66 (s, 1H);
¹³C NMR (DMSO-d₆): δ=27.0, 27.2, 44.7, 49.2, 82.8, 83.4, 125.9, 148.0, 149.5, 149.6, 150.2, 151.0, 154.0;
MS (ESI) m/z 607.3 [M+H]+;
HRMS: calc. C28H43N6O9 [M+H]+ 607.3092, obs. 607.3088.

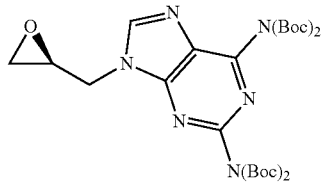

N²,N²—N⁶,N⁶-Tetra(tert-butoxycarbonyl)-9-{[(2S)-oxiran-2-yl] methyl}2,6-diaminopurine yield=84%; white solid; R$_f$=0.42 (EP/AcOEt, 4/6, v/v);
¹H NMR (DMSO-d₆): δ=1.36 (s, 36H), 2.44 (dd, 1H, 2J=4.8 Hz, 3J=2.7 Hz), 2.83 (m, 1H), 3.45 (m, 1H), 4.40 (dd, 1H, 2J=15.0 Hz, 3J=5.7 Hz), 4.67 (dd, 1H, 2J=14.9 Hz, 3J=3.2 Hz), 8.66 (s, 1H);
¹³C NMR (DMSO-d₆): δ=27.0, 27.2, 44.7, 49.2, 82.8, 83.4, 125.9, 148.0, 149.5, 149.6, 150.2, 151.0, 154.0;
MS (ESI) m/z 607.3 [M+H]+;
HRMS: calc. C28H43N6O9 [M+H]+ 607.3092, obs. 607.3082.

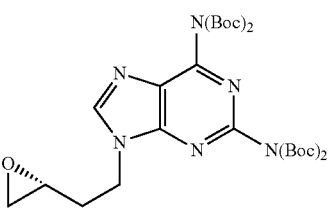

N²,N²—N⁶,N⁶-Tetra(tert-butoxycarbonyl)-9-{[(2R)-oxiran-2-yl] ethyl}2,6-diaminopurine yield=90%; colorless oil; R$_f$=0.34 (CH₂Cl₂/MeOH, v/v);
¹H NMR (DMSO-d₆): δ=1.35 (s, 36H), 1.95-2.16 (m, 1H), 2.13-2.20 (m, 1H), 2.27 (m, 1H), 2.56 (m, 1H), 2.93-2.96 (m, 1H), 4.45 (t, 2H), 8.72 (s, 1H);

¹³C NMR (DMSO-d₆): δ=27.0, 27.2, 31.9, 45.1, 49.2, 82.8, 83.4, 126.3, 148.0, 149.4, 149.5, 150.3, 150.7, 153.9;

MS (ESI) m/z 621.3 [M+H]+; 643.3 [M+Na]+; 1263.6 [M+2Na]+.

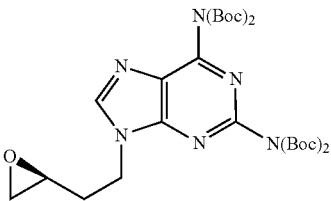

N²,N²—N⁶,N⁶-Tetra(tert-butoxycarbonyl)-9-{[(2S)-oxiran-2-yl] ethyl}2,6-diaminopurine yield=89%; white solid; R$_f$=0.23 (CH₂Cl₂/MeOH, 95/5, v/v);

¹H NMR (DMSO-d₆): δ=1.35 (s, 36H), 1.97-2.04 (m, 1H), 2.13-2.23 (m, 1H), 2.26 (m, 1H), 2.56 (m, 1H), 2.94 (m, 1H), 4.44 (t, 2H), 8.71 (s, 1H);

¹³C NMR (DMSO-d₆): δ=27.0, 27.2, 31.9, 41.1, 45.1, 49.1, 82.8, 83.4, 126.3, 148.0, 149.4, 149.5, 150.2, 150.7, 153.9;

MS (ESI) m/z 621.33 [M+H]+; 643.31 [M+Na]+.

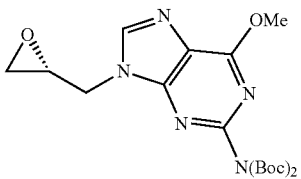

N²,N²-Bis(tert-butoxycarbonyl)-6-O-methyl_9-{[(2R)-oxiran-2-yl] methyl}2-aminopurine yield=74%; white solid; R$_f$=0.2 (AcOEt);

¹H NMR (DMSO-d₆): δ=1.39 (s, 18H), 2.5 (1H partially masked by DMSO), 2.81 (m, 1H), 3.40 (m, 1H), 4.1 (s, 3H), 4.34 (dd, 1H, 2J=15.0 Hz, 3J=5.7 Hz), 4.54 (dd, 1H, 2J=15.0 Hz, 3J=3.3 Hz), 8.4 (s, 1H);

¹³C NMR (DMSO-d₆): δ=27.3, 44.7, 44.8, 49.3, 54.2, 82.6, 118.7, 144.9, 150.3, 151.0, 152.7, 160.6;

MS (ESI) m/z 422.2 [M+H]+;

HRMS: calc. C19H28N5O6 [M+H]+ 422.2040, obs. 422.2034.

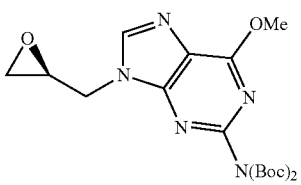

N²,N²-Bis(tert-butoxycarbonyl)-6-O-methyl_9-{[(2S)-oxiran-2-yl]methyl}2-aminopurine yield=76%; white solid; R$_f$=0.2 (AcOEt);

¹H NMR (DMSO-d₆): δ=1.39 (s, 18H), 2.5 (1H partially masked by DMSO), 2.81 (m, 1H), 3.41 (m, 1H), 4.1 (s, 3H), 4.34 (dd, 1H, 2J=15.0 Hz, 3J=5.4 Hz), 4.54 (dd, 1H, 2J=15.0 Hz, 3J=3.3 Hz), 8.4 (s, 1H);

¹³C NMR (DMSO-d₆): δ=27.3, 44.7, 44.9, 49.3, 54.3, 82.7, 118.7, 144.9, 150.3, 151.0, 152.7, 160.6;

MS (ESI) m/z 422.2 [M+H]+;

HRMS: calc. C19H28N5O6 [M+H]+ 422.2040, obs. 422.2047.

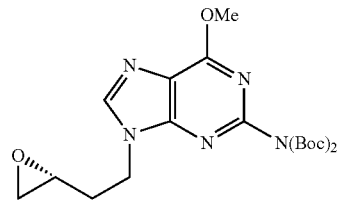

N²,N²-Bis(tert-butoxycarbonyl)-6-O-methyl_9-{[(2R)-oxiran-2-yl]ethyl}2-aminopurine yield=79%; colorless oil; R$_f$=0.37 (CH₂Cl₂/MeOH 95/5, v/v);

[α]²⁰$_D$=+17 (c 0.01, HCCl3);

¹H NMR (DMSO-d₆): δ=1.38 (s, 18H), 1.90-2.10 (2m, 2H), 2.28 (m, 1H), 2.58 (m, 1H), 2.93 (m, 1H), 4.06 (s, 3H), 4.37 (t, 2H), 8.45 (s, 1H);

¹³C NMR (DMSO-d₆): δ=27.3, 32.1, 45.3, 49.1, 54.2, 82.6, 118.9, 144.8, 150.3, 150.7, 152.6, 160.5;

MS (ESI) m/z 436.22 [M+H]+; 893.42 [2M+Na]+.

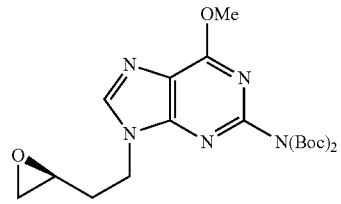

N²,N²-Bis(tert-butoxycarbonyl)-6-O-methyl_9-{[(2S)-oxiran-2-yl]ethyl}2-aminopurine yield=78%; colorless oil; R$_f$=0.36 (CH₂Cl₂/MeOH 95/5, v/v);

[α]²⁰$_D$=−26.7 (c 0.01, DCM);

¹H NMR (DMSO-d₆): δ=1.38 (s, 18H), 1.93-2.19 (2m, 2H), 2.29 (m, 1H), 2.58 (m, 1H, partially masked by DMSO), 2.94 (m, 2H), 4.06 (s, 3H), 4.37 (t, 1H), 8.45 (s, 1H);

¹³C NMR (DMSO-d₆): δ=27.3, 32.10, 45.3, 49.1, 54.2, 82.6, 118.9, 144.8, 150.3, 151.0, 152.6, 160.5;

MS (ESI) m/z 436.22 [M+H]+; 458.20 [M+Na]+; 893.42 [2M+Na]+.

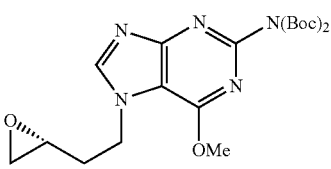

N²,N²-Bis(tert-butoxycarbonyl)-6-O-methyl-N7-{[(2R)-oxiran-2-yl]ethyl}2-aminopurine yield=19%; colorless oil; $R_f$=0.27 (CH$_2$Cl$_2$/MeOH, 95/5, v/v); ¹H NMR (CdCl$_3$): δ=1.39 (s, 18H), 1.90-2.0 (m, 1H), 2.25-2.31 (m, 1H), 2.41-2.45 (m, 1H), 2.49-2.53 (m, 1H), 2.76-2.79 (m, 1H), 4.14 (s, 3H), 4.43-4.57 (m, 2H), 8.06 (s, 1H); ¹³C NMR (CDCl$_3$): δ=27.9, 34.1, 44.7, 46.9, 48.9, 54.6, 82.9, 111.2, 146.3, 151.2, 151.9, 157.4, 162.9; MS (ESI) m/z 436.22 [M+H]+.

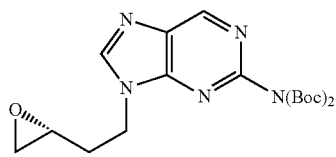

N²,N²-Bis(tert-butoxycarbonyl)-9{[(2R)-oxiran-2-yl]ethyl}2-aminopurine yield=71%; colorless oil; $R_f$=0.40 (CH$_2$Cl$_2$/MeOH, 95/5, v/v); ¹H NMR (CdCl$_3$): δ=1.43 (s, 18H), 1.93-2.01 (m, 1H), 2.30-2.42 (m, 1H), 2.43-2.46 (m, 1H), 2.74-2.78 (m, 1H), 2.90-2.97 (m, 1H), 4.43-4.48 (m, 2H), 8.16 (s, 1H), 9.12 (s, 1H); ¹³C NMR (CDCl$_3$): δ=27.9, 29.7, 32.6, 41.2, 46.8, 49.3, 83.3, 146.2, 149.6; MS (ESI) m/z 406.21 [M+H]+.

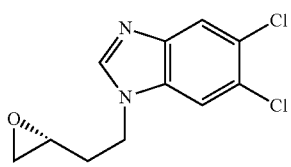 [SMILES: Clc1cc2ncn(CC[C@@H]3CO3)c2cc1Cl]

N-1-{[(2R)-oxiran-2-yl]ethyl}5,6-dichlorobenzimidazole

Yield=29%; colorless oil, $R_f$=0.47 (CH$_2$Cl$_2$/MeOH, 95/5, v/v); ¹H NMR (CDCl$_3$): δ=1.80-1.96 (m, 1H), 2.30-2.40 (m, 1H), 2.48-2.53 (m, 1H), 2.65-2.72 (m, 1H), 2.87-2.92 (m, 1H), 4.38 (t, 2H), 7.57 (s, 1H), 7.93 (s, 1H), 8.25 (s, 1H). MS (ESI) m/z 257.003 [M+H]+; MS (ESI) m/z 256.95 [M−H]⁻;

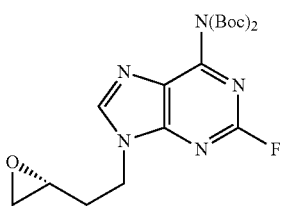

N⁶,N⁶-Bis(tert-butoxycarbonyl)-9{[(2R)-oxiran-2-yl]ethyl}6-amino-2-fluoro purine Yield=50%; colorless oil; $R_f$=0.43 (CH$_2$Cl$_2$/MeOH, 95/5, v/v); ¹H NMR (CDCl$_3$): δ=1.46 (s, 18H), 1.85-1.96 (m, 1H), 2.27-2.42 (m, 1H), 2.45-2.51 (m, 1H), 2.76 (m, 1H), 2.92-2.96 (m, 1H), 4.39 (t, 2H), 7.26 (s, 1H), 8.07 (s, 1H); ¹³C NMR (CDCl$_3$): δ=26.7, 31.4, 40.5, 45.8, 48.2, 83.3, 125.9, 144.1, 148.9, 151.0, 151.1, 154.0, 154.1, 156.0, 157.7; MS (ESI) m/z 424.2.

1.2.3. General Procedure for Synthesizing Compounds of Formula IV

Bis(trimethylsilyl)acetamide (N,O—BSA) (6.4 eq.) is added to a solution of diethyl phosphite (6 eq.) in anhydrous toluene (1 mL/mmol) and under argon. The reaction medium is heated at reflux for 3 h then cooled to room temperature and then to −60° C. A solution of compound III prepared according to example 1.2 (1 eq.) in anhydrous dichloromethane is transferred by cannula to the preceding reaction medium, then a solution of BF$_3$.OEt$_2$ (6 eq.) is added. The reaction medium is maintained under stirring at −60° C. for 3 h and then left at room temperature. After stirring overnight, the reaction medium is concentrated at a reduced pressure. The residue is purified on a silica gel column (CH$_2$Cl$_2$/MeOH, 0-10%) leading, after the evaporation of the pooled fractions, to the expected compound (formula IV).

The following compounds of formula (IV) were synthesized:

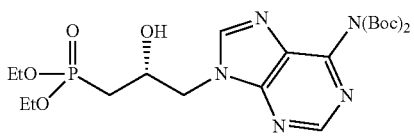

N⁶,N⁶-Bis(tert-butoxycarbonyl)-9-[(2R)-2-hydroxy-3-diethylphosphonopropyl]adenine yield=62.6%; white solid; $R_f$=0.42 (CH$_2$Cl$_2$/MeOH, 90/10, v/v);
[α]²⁰$_D$=+7.8 (c 1.02, MeOH);
¹H NMR (DMSO-d6): δ=1.22 (t, 6H), 1.38 (s, 18H), 1.84-2.08 (m, 2H), 3.90-4.04 (m, 4H), 4.24 (m, 2H), 4.46 (m, 1H), 5.50 (d, 1H), 8.52 (s, 1H), 8.83 (s, 1H);
¹³C NMR (CDCl$_3$): δ=16.4, 16.5, 27.9, 30.9, 49.8, 62.4, 62.5, 65.3, 84.0, 128.7, 146.4, 150.4, 150.6, 152.0, 153.7;
³¹P NMR (DMSO-d6): δ=28.1;
MS (ESI) m/z 530.3 [M+H]⁺;
HRMS: calc. C$_{22}$H$_{37}$N$_5$O$_8$P [M+H]⁺ 530.2380, obs. 530.2391.

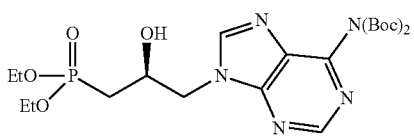

N⁶,N⁶-Bis(tert-butoxycarbonyl)-9-[(2S)-2-hydroxy-3-diethylphosphonopropyl]adenine yield=64.2%; white solid; $R_f$=0.42 (CH$_2$Cl$_2$/MeOH, 90/10, v/v);
[α]²⁰$_D$=−6.9 (c 1.01, MeOH);

$^1$H NMR (DMSO-d6): δ=1.23 (t, 6H), 1.38 (s, 18H), 1.85-2.24 (m, 2H), 4.01 (m, 4H), 4.23 (m, 2H), 4.46 (m, 1H), 5.48 (d, 1H), 8.51 (s, 1H), 8.83 (s, 1H);

$^{13}$C NMR (CDCl$_3$): δ=16.4, 16.5, 27.9, 31.0, 49.8, 62.4, 62.5, 65.4, 83.9, 128.6, 146.4, 150.4, 150.6, 152.0, 153.7;

$^{31}$P NMR (DMSO-d6): δ=28.1;

MS (ESI) m/z 530.3 [M+H]$^+$;

HRMS: calc. C$_{22}$H$_{37}$N$_5$O$_8$P [M+H]$^+$ 530.2380, obs. 530.2375.

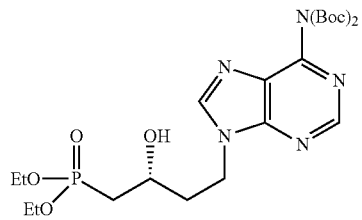

N$^6$,N$^6$-Bis(tert-butoxycarbonyl)-9-[(2R)-2-hydroxy-4-diethyl phosphonobutyl]adenine yield=68%; white solid; R$_f$=0.15 (CH$_2$Cl$_2$/MeOH, 95/5, v/v);

$^1$H NMR (DMSO-d6): δ=1.12-1.26 (m, 6H), 1.37 (s, 18H), 1.85-2.10 (m, 3H), 2.20 (m, 1H), 3.74 (m, 1H), 3.80-4.00 (m, 4H), 4.41 (m, 2H), 5.08 (d, 1H), 8.61 (s, 1H), 8.83 (s, 1H);

$^{13}$C NMR (DMSO-d6): δ=16.0, 16.1, 27.2, 32.6, 34.3, 36.8, 36.9, 60.6, 60.7, 60.8, 60.9, 62.9, 83.1, 127.7, 146.9, 148.8, 149.9, 151.2, 153.0;

$^{31}$P NMR (DMSO-d6): δ=28.5; MS (ESI) m/z 544.23 [M+H]$^+$.

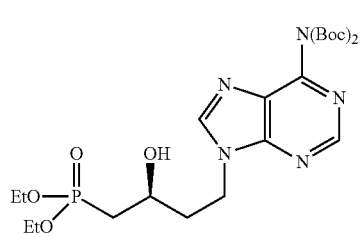

N$^6$,N$^6$-Bis(tert-butoxycarbonyl)-9-[(2S)-2-hydroxy-4-diethyl phosphonobutyl]adenine yield=69%; white solid; R$_f$=0.17 (CH$_2$Cl$_2$/MeOH, 95/5, v/v);

$^1$H NMR (DMSO-d6): δ=1.12-1.16 (m, 6H), 1.37 (s, 18H), 1.85-2.05 (m, 3H), 2.20 (m, 1H), 3.73 (m, 1H), 3.85-3.95 (m, 4H), 4.39 (m, 2H), 5.08 (d, 1H), 8.61 (s, 1H), 8.83 (s, 1H);

$^{13}$C NMR (DMSO-d6): δ=16.0, 16.1, 27.2, 32.6, 34.3, 36.8, 36.9, 60.6, 60.7, 60.8, 60.9, 63.0, 83.1, 127.7, 146.9, 148.8, 149.9, 151.2, 153.0;

$^{31}$P NMR (DMSO-d6): δ=28.5;

MS (ESI) m/z 544.26 [M+H]$^+$.

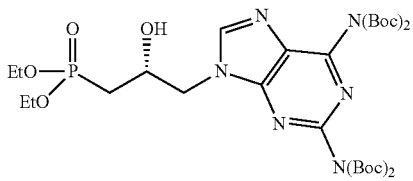

N$^2$,N$^2$—N$^6$,N$^6$-Tetra(tert-butoxycarbonyl)-9-[(2R)-2-hydroxy-3-diethylphosphonopropyl] 2,6-diaminopurine yield=36%; white solid; R$_f$=0.18 (CH$_2$Cl$_2$/MeOH, 95/5, v/v);

$^1$H NMR (DMSO-d6): δ=1.22 (pt, 6H, 2×CH$_3$), 1.36 (s, 36H), 2.00 (m, 2H), 3.99 (m, 4H, 2×CH$_2$), 4.22 (m, 1H), 4.47 (m, 1H), 5.51 (d, 1H, J=5.1 Hz), 8.56 (s, 1H); 31P NMR (DMSO-d6): 27.9;

$^{13}$C NMR (DMSO-d6): δ=16.0, 16.1, 27.0, 27.2, 30.3, 32.1, 60.8, 60.9, 61.0, 61.1, 64.0, 82.7, 83.3, 126.1, 148.5, 149.3, 149.6, 150.2, 150.7, 154.0;

MS (ESI) m/z 745.3 [M+H]+;

HRMS: calc. C32H54N6O12P [M+H]+ 745.3537, obs. 745.3543.

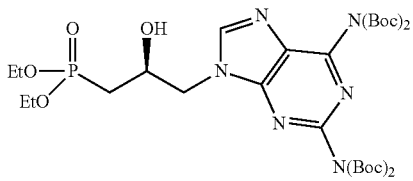

N$^2$,N$^2$—N$^6$,N$^6$-Tetra(tert-butoxycarbonyl)-9-[(2S)-2-hydroxy-3-diethylphosphonopropyl] 2,6-diaminopurine yield=66%; white solid; R$_f$=0.21 (CH$_2$Cl$_2$/MeOH, 95/5, v/v);

$^1$H NMR (DMSO-d$_6$): δ=1.22 (pt, 6H, 2×CH$_3$), 1.36 (s, 36H), 2.00 (m, 2H), 3.99 (m, 4H, 2×CH$_2$), 4.20 (m, 1H), 4.47 (m, 1H), 5.51 (d, 1H, J=5.1 Hz), 8.56 (s, 1H); 31P NMR (DMSO-d6): 27.9;

$^{13}$C NMR (DMSO-d$_6$): δ=16.0, 16.1, 27.1, 27.2, 30.3, 32.1, 60.8, 60.9, 61.0, 61.1, 63.9, 63.7, 82.7, 83.3, 126.1, 148.5, 149.3, 149.6, 150.2, 150.7, 154.0;

MS (ESI) m/z 745.3 [M+H]+;

HRMS: calc. C32H54N6O12P [M+H]+ 745.3537, obs. 745.3531.

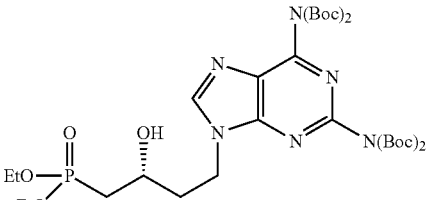

N², N²—N⁶, N⁶-Tetra(tert-butoxycarbonyl)-9-[(2R)-2-hydroxy-4-diethylphosphonobutyl] 2,6-diaminopurine yield=70%; white solid; $R_f$=0.42 (CH$_2$Cl$_2$/MeOH, 9/1, v/v);

¹H NMR (DMSO-d6): δ=1.18 (t, 6H), 1.36 (s, 36H), 1.90-2.10 (m, 3H), 2.14 (m, 1H), 3.70-3.96 (2m, 3H), 4.36 (m, 1H), 5.11 (d, 1H), 8.67 (s, 1H); 31P NMR (DMSO-d6): 28.4;

¹³C NMR (DMSO-d6): δ=16.0, 16.1, 27.0, 27.2, 32.6, 34.4, 60.6, 60.7, 60.8, 60.9, 63.1, 82.8, 83.3, 126.2, 147.9, 149.4, 149.6, 150.3, 150.7, 153.7;

MS (ESI) m/z 759.37 [M+H]+;

HRMS: calc. C33H56N6O12P [M+H]+ 759.3694, obs. 759.3687.

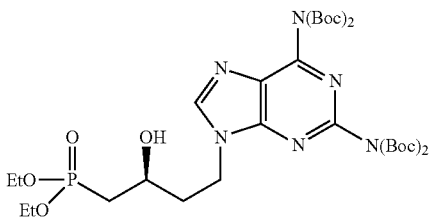

N², N²—N⁶, N⁶-Tetra(tert-butoxycarbonyl)-9-[(2S)-2-hydroxy-4-diethylphosphonobutyl] 2,6-diaminopurine yield=70%; white solid; $R_f$=0.24 (CH$_2$Cl$_2$/MeOH, 95/5, v/v);

¹H NMR (DMSO-d6): δ=1.18 (t, 6H), 1.36 (s, 36H), 1.85-2.20 (2m, 4H), 3.80-4.05 (2m, 4H), 4.36 (m, 1H), 5.11 (d, 1H), 8.67 (s, 1H); 31P NMR (DMSO-d6): 28.4; 13C NMR (DMSO-d6): δ=16.0, 16.1, 27.0, 27.2, 32.6, 34.4, 60.6, 60.7, 60.8, 60.9, 63.1, 82.8, 83.3, 126.2, 147.9, 149.3, 149.6, 150.3, 150.7, 153.8;

MS (ESI) m/z 759.37 [M+H]+.

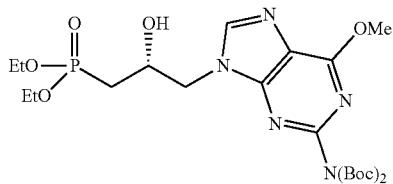

N², N²-Bis(tert-butoxycarbonyl)-6-O-methyl-9-[(2R)-2-hydroxy-3-diethylphosphono propyl]2-aminopurine yield=40.7%; white solid; $R_f$=0.16 (CH$_2$Cl$_2$/MeOH, 95/5, v/v);

¹H NMR (DMSO-d$_6$): δ=1.22 (pt, 6H, 2×CH$_3$), 1.38 (s, 18H), 1.98 (m, 2H), 4.05 (m, 9H), 4.39 (m, 1H), 5.41 (d, 1H, J=5.1 Hz), 8.30 (s, 1H);

³¹P NMR (DMSO-d6): 28.1; 13C NMR (DMSO-d$_6$): δ=16.0, 16.1, 27.3, 54.2, 60.8, 60.9, 61.0, 61.1, 64.0, 64.1, 72.7, 82.5, 118.8, 145.5, 150.3, 152.7, 160.5;

MS (ESI) m/z 560.3 [M+H]+;

HRMS: calc. C$_{23}$H$_{39}$N5O9P [M+H]+ 560.2485, obs. 560.2481.

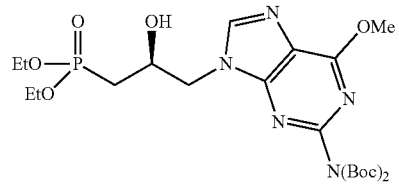

N², N²-Bis(tert-butoxycarbonyl)-6-O-methyl-9-[(2S)-2-hydroxy-3-diethylphosphono propyl]2-aminopurine yield=43%; white solid; $R_f$=0.16 (CH$_2$Cl$_2$/MeOH, 95/5, v/v);

¹H NMR (DMSO-d$_6$): δ=1.23 (pt, 6H, 2×CH$_3$), 1.39 (s, 18H), 2.00 (m, 2H), 4.08 (m, 9H), 4.40 (m, 1H), 5.43 (d, 1H, J=5.4 Hz), 8.30 (s, 1H);

³¹P NMR (DMSO-d6): 28.1;

MS (ESI) m/z 560.3 [M+H]+; 582.23 [M+Na]+.

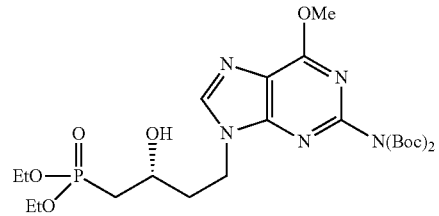

N², N²-Bis(tert-butoxycarbonyl)-6-O-methyl-9-[(2R)-2-hydroxy-4-diethylphosphono butyl 2-aminopurine yield=41%; white solid; $R_f$=0.16 (CH$_2$Cl$_2$/MeOH, 95/5, v/v);

[α]$^{20}_D$=+14 (c 0.01, DCM);

¹H NMR (DMSO-d$_6$): δ=1.17 (pt, 6H, 2×CH$_3$), 1.39 (s, 18H), 1.84-2.00 (m, 3H), 2.09 (m, 1H), 3.78 (M, 1H), 3.94 (m, 4H), 4.06 (s, 3H), 4.28 (m, 2H), 5.07 (d, 1H, J=5.1 Hz), 8.39 (s, 1H); 31P NMR (DMSO-d6): 28.5;

¹³C NMR (DMSO-d$_6$): δ=16.0, 16.1, 27.3, 54.2, 60.6, 60.7, 60.8, 60.9, 63.0, 82.5, 118.9, 144.7, 150.4, 150.7, 152.5, 160.4;

MS (ESI) m/z 574.26 [M+H]+, 596.25 [M+Na]+;

HRMS: calc. C24H40N5O9NaP [M+Na]+ 596.2461, obs. 596.2460.

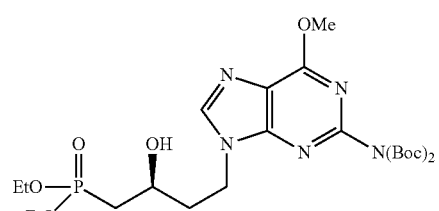

$N^2,N^2$-Bis(tert-butoxycarbonyl)-6-O-methyl-9-[(2S)-2-hydroxy-4-diethylphosphono butyl]2-aminopurine yield=48%; white solid; $R_f$=0.17 (CH$_2$Cl$_2$/MeOH, 95/5, v/v);
$[\alpha]^{20}_D$=−15.3 (c 0.0098, DCM);
$^1$H NMR (DMSO-d$_6$): δ=1.17 (t, 6H, 2×CH$_3$), 1.39 (s, 18H), 185-2.0 (m, 3H), 2.10 (m, 1H), 3.78 (m, 1H), 3.94 (m, 4H), 4.06 (s, 3H), 4.29 (m, 2H), 5.08 (d, 1H, J=5.0 Hz), 8.40 (s, 1H);
$^{13}$P NMR (DMSO-d6): δ=28.5;
$^{13}$C NMR (DMSO-d$_6$): δ=16.0, 16.1, 27.3, 32.5, 34.4, 54.2, 60.6, 60.7, 60.8, 60.9, 63.0, 82.6, 118.9, 144.8, 150.4, 150.7, 152.5, 160.5;
MS (ESI) m/z 574.26 [M+H]+, 596.25 [M+Na]+.

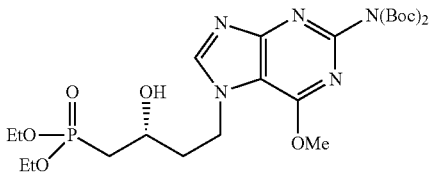

$N^2,N^2$-Bis(tert-butoxycarbonyl)-6-O-methyl-7-[(2R)-2-hydroxy-4-diethyl phosphonobutyl 2-aminopurine Yield=39%; white solid; $R_f$=0.20 (CH$_2$Cl$_2$/MeOH, 95/5, v/v); $^1$H NMR (CDCl$_3$): δ=1.28 (pt, 6H, 2×CH$_3$), 1.44 (s, 18H), 1.83-2.05 (2m, 4H), 3.80 (m, 1H), 3.97 (m, 1H), 4.04-4.15 (m, 7H), 4.49 (m, 2), 8.08 (s, 1H); 31P NMR (CDCl$_3$): 29.2; $^{13}$C NMR (CDCl$_3$: δ=16.3, 16.4, 27.9, 29.7, 54.5, 62.1, 82.9, 146.9, 151.3, 157.5, 163.0; MS (ESI) m/z 574.26 [M+H]+, 1147.52 [2M+H]+; HRMS: calc. C24H41N5O9P [M+H]+ 574.2642, obs. 574.2648.

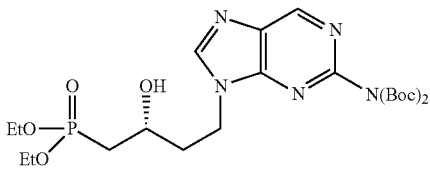

$N^2,N^2$-Bis(tert-butoxycarbonyl)-9[(2S)-2-hydroxy-4-diethylphosphonobutyl]2-aminopurine Yield=73%; white solid; $R_f$=0.22 (CH$_2$Cl$_2$/MeOH, 95/5, v/v); $^1$H NMR (CDCl$_3$): δ=1.30 (pt, 6H, 2×CH$_3$), 1.46 (s, 18H), 1.85-2.17 (2m, 4H), 3.87 (m, 1H), 4.09 (m, 4H), 4.90 (m, 2H), 8.37 (s, 1H), 9.13 (s, 1H); $^{31}$P NMR (CDCl$_3$): 29.0; $^{13}$C NMR (CDCl$_3$: δ=16.6, 16.7, 28.2, 33.1, 34.5, 37.8, 37.9, 40.9, 62.4, 63.4, 83.6, 147.2, 149.8, 151.4, 153.1; MS (ESI) m/z 566.24 [M+Na]+.

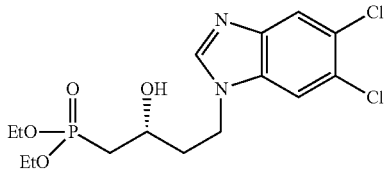 [SMILES: CCOP(=O)(C[C@H](O)CCn1cnc2cc(Cl)c(Cl)cc21)OCC]

N-1-[(2R)-2-hydroxy-4-diethylphosphonobutyl] 5,6-dichlorobenzimidazole

Yield=68%; white solid; $R_f$=0.24 (CH$_2$Cl$_2$/MeOH, 95/5, v/v); $^1$H NMR (CDCl$_3$): δ=1.23 (m, 6H), 1.80-2.05 (m, 8H), 3.83 (m, 1H), 4.04 (m, 4H), 4.20-4.41 (2m, 2H), 7.55 (s, 1H), 7.82 (s, 1H), 7.965 (s, 1H); $^{13}$C NMR (CDCl$_3$: δ=16.2, 16.3, 22.5, 33.0, 34.4, 37.6, 37.8, 41.5, 62.0, 62.9, 63.0, 111.2, 121.3, 126.2, 127.0, 132.9, 142.9, 145.2, 172.9; $^{31}$P NMR (CDCl$_3$): δ=29.0; MS (ESI) m/z 395.07 [M+H]+.

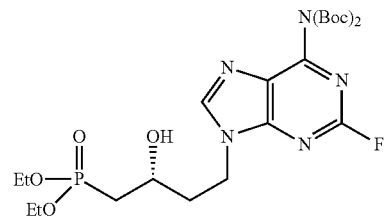

$N^6,N^6$-Bis(tert-butoxycarbonyl)-9-[(2R)-2-hydroxy-4-diethylphosphonobutyl]-6-amino-2-fluoropurine Yield=89%; white solid; $R_f$=0.25 (CH$_2$Cl$_2$/MeOH, 95/5, v/v); $^1$H NMR (CDCl$_3$): δ=1.30 (pt, 6H), 1.49 (s, 18H), 1.90-2.2 (2m, 5H), 3.95 (m, 1H), 4.05-4.17 (m, 4H), 4.45 (m, 2H), 8.25 (s, 1H); 31P NMR (CDCl$_3$): 29.1; $^{13}$C NMR (CDCl$_3$: δ=15.3, 15.4, 26.7, 31.8, 33.2, 36.3, 36.4, 40.1, 61.2, 62.3, 62.4, 83.4, 144.8, 149.0, 150.7, 150.9, 154.0, 155.8; MS (ESI) m/z 562.25 [M+H]+.

1.2.4 General Procedure for Synthesizing Compounds of Formula V and VIII

Bromotrimethylsilane (TMSBr) (5-10 eq.) is added to a solution of the compound of formula IV (1 eq.) in DMF or anhydrous acetonitrile (2 mL: 0.1 mmol) at 0° C. under argon. The reaction mixture is stirred at room temperature for 24 h. Then, water (5 mL) is added, and the stirring is continued at room temperature for 1 h. The reaction medium is concentrated at reduced pressure, and the residue is either purified on a silica gel column (isocratic: iPrOH/H$_2$O/NH$_4$OH 7/2/1) or a reverse phase column (H$_2$O/MeOH, 0-25%) leading, after evaporation of the pooled fractions, to the expected phosphonic acid. The sodium salts of the expected compound (of formula V) are isolated after percolation through a Dowex® Na+ exchange resin (elution with water).

The following compounds of formula (V) were synthesized:

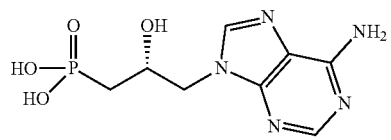 [SMILES: Nc1ncnc2c1ncn2C[C@@H](O)CP(=O)(O)O]

N-9-[(2R)-2-hydroxy-3-phosphonopropyl] adenine yield=44.8%; lyophilizate; $R_f$=0.66 (iPrOH/H$_2$O/NH$_4$OH 7/4/2);
$^1$H NMR (D2O): δ=1.83-1.95 (2m, 2H), 4.05-4.16 (m, 1H), 4.21-4.38 (m, 2H), 7.96 (s, 1H), 8.00 (s, 1H);

<sup>13</sup>C NMR (D2O): δ=32.4, 34.1, 49.8, 49.9, 66.2, 117.7, 142.7, 148.4, 151.7, 154.8;
<sup>31</sup>P NMR (D2O): δ=19.8; MS (ESI) m/z 272.06 [M+H]⁺; HRMS: calc. C8H11N5O4P [M+H]⁺ 272.0549, obs. 272.0551.

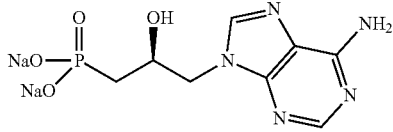

N-9-[(2S)-2-hydroxy-3-phosphonopropyl] adenine yield=47%; lyophilizate; R<sub>f</sub>=0.52 (iPrOH/H₂O/NH₄OH 7/4/2);
<sup>1</sup>H NMR (D2O): δ=1.77-1.97 (2m, 2H), 4.06-4.17 (m, 1H), 4.21-4.40 (m, 2H), 8.00 (s, 1H), 8.02 (s, 1H);
<sup>13</sup>C NMR (D2O): δ=32.4, 34.1, 49.8, 49.9, 66.3, 117.8, 142.8, 148.6, 151.9, 155.0;
<sup>31</sup>P NMR (D2O): δ=19.7;
MS (ESI) m/z 318.04 [M+H]⁺; 296.05 [M-Na+2H]⁺; 274.07 [M-2Na+3H]⁺;
HRMS: calc. C8H11N5O4Na2P [M+H]⁺ 318.0344, obs. 318.0349.

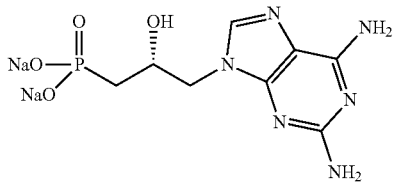

N-9-[(2R)-2-hydroxy-3-phosphonopropyl]2,6-di-amino purine yield=64%; lyophilizate; R<sub>f</sub>=0.46 (iPrOH/H₂O/NH₄OH 7/2/1);
<sup>1</sup>H NMR (D2O): δ=1.6'7-1.8ç (m, 2H), 3.96-4.10 (m, 1H), 4.20-4.30 (m, 2H), 7.78 (s, 1H);
<sup>13</sup>C NMR (D2O): δ=32.5, 34.2, 49.4, 49.6, 66.6, 140.6, 155.7, 159.5;
<sup>31</sup>P NMR (D2O): δ=18.7; MS (ESI) m/z 289.08 [M-2Na+3H]⁺, 311.06 [M-Na+2H]⁺, 333.05 [M+H]⁺;
HRMS: calc. C8H12N6O4Na2P [M+H]⁺ 333.0453, obs. 333.0460.

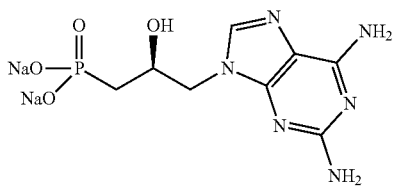

N-9-[(2S)-2-hydroxy-3-phosphonopropyl]2,6-di-amino purine yield=70.5%; lyophilizate; R<sub>f</sub>=0.56 (iPrOH/H₂O/NH₄OH 7/4/2);
<sup>1</sup>H NMR (D2O): δ=1.54-1.80 (m, 2H), 3.93-4.03 (m, 1H), 4.17-4.28 (m, 2H), 7.80 (s, 1H);
<sup>13</sup>C NMR (D2O): δ=32.8, 34.4, 49.6, 49.8, 67.1, 112.7, 140.6, 151.0, 155.8, 159.7;
<sup>31</sup>P NMR (D2O): δ=17.5;
MS (ESI) m/z 289.08 [M-2Na+3H]⁺, 311.06 [M-Na+2H]⁺, 333.05 [M+H]⁺; 355.03 [M+Na]⁺;
HRMS: calc. C8H12N6O4Na2P [M+H]⁺ 333.0453, obs. 333.0450.

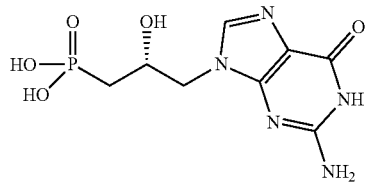 [SMILES: Nc1nc2c(ncn2C[C@@H](O)CP(=O)(O)O)c(=O)[nH]1]

N-9-[(2R)-2-hydroxy-3-phosphonopropyl]guanine yield=68%; lyophilizate; R<sub>f</sub>=0.44 (iPrOH/H₂O/NH₄OH 7/4/2);
<sup>1</sup>H NMR (D2O): δ=1.80-2.00 (m, 2H), 3.93-4.05 (m, 1H), 4.18-4.33 (m, 2H), 7.76 (s, 1H);
<sup>13</sup>C NMR (D2O): δ=32.6, 33.9, 49.6, 49.7, 66.2, 115.7, 140.6, 153.6, 158.8;
<sup>31</sup>P NMR (D2O): δ=20.1;
MS (ESI) m/z 288.05 [M-H]⁻, 577.11 [2M-H]⁻;
HRMS: calc. C8H11N5O5P [M-H]⁻ 288.0498, obs. 288.0498.

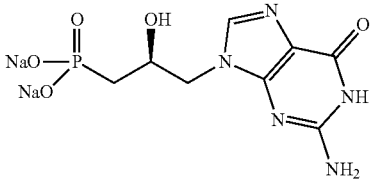

N-9-[(2S)-2-hydroxy-3-phosphono propyl]guanine yield=70.5%; lyophilizate; R<sub>f</sub>=0.57 (iPrOH/H₂O/NH₄OH 7/4/2);
<sup>1</sup>H NMR (D2O): δ=1.78-1.97 (m, 2H), 3.93-4.05 (m, 1H), 4.19-4.32 (m, 2H), 7.76 (s, 1H);
<sup>13</sup>C NMR (D2O): δ=32.3, 34.1, 49.5, 49.7, 66.2, 115.6, 140.6, 151.6, 153.5, 158.8;
31P NMR (D2O): δ=19.9;
MS (ESI) m/z 290.07 [M-2Na+3H]⁺, 312.05 [M-Na+2H]⁺; 334.03 [M+H]⁺;
HRMS: calc. C8H11N5O5Na2P [M+H]⁺ 334.0293, obs. 334.0302.

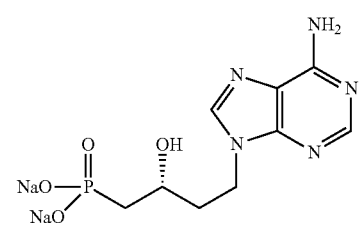

N-9[(2R)-2-hydroxy-4-phosphonobutyl]adenine yield=99%; lyophilizate; R$_f$=0.21 (iPrOH/H$_2$O/NH$_4$OH 7/2/1);

$^1$H NMR (D$_2$O): δ=1.79-1.99 (m, 3H), 2.11-2.24 (m, 1H), 3.87-4.00 (m, 1H), 4.16-4.26 (m, 2H), 7.96 (s, 1H), 7.99 (s, 1H);

$^{13}$C NMR (D$_2$O): δ=35.5, 36.7, 36.9, 37.0, 40.9, 65.5, 117.9, 142.2, 148.3, 151.8, 154.9;

$^{31}$P NMR (D$_2$O): δ=20.7;

MS (ESI) m/z 332.02 [M+H]$^+$; 310.04 [M−Na+2H]$^+$; 288.07 [M−2Na+3H]$^+$;

HRMS: calc. C9H15N5O4P [M−2Na+3H]$^+$ 288.0862, obs. 288.0867.

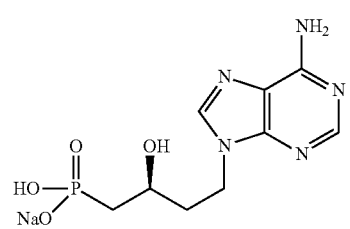

N-9[(2S)-2-hydroxy-4-phosphonobutyl]adenine yield=69%; lyophilizate; R$_f$=0.26 (iPrOH/H$_2$O/NH$_4$OH 7/2/1);

$^1$H NMR (D$_2$O): δ=1.78-1.98 (m, 3H), 2.11-2.22 (m, 1H), 3.87-3.98 (m, 1H), 4.15-4.25 (m, 2H), 7.96 (s, 1H), 7.98 (s, 1H);

$^{13}$C NMR (D$_2$O): δ=35.5, 36.7, 36.8, 36.9, 40.9, 65.5, 117.9, 142.2, 148.3, 151.8, 154.9;

$^{31}$P NMR (D$_2$O): δ=20.6;

MS (ESI) m/z 310.04 [M+H]$^+$; 288.07 [M−Na+2H]$^+$;

HRMS: calc. C9H15N5O4P [M−Na+2H]$^+$ 288.0862, obs. 288.0860.

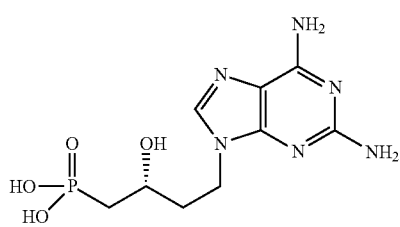 [SMILES: Nc1nc(N)c2ncn(CC[C@@H](O)CP(=O)(O)O)c2n1]

2,6-diAmino-9-[(2R)-2-hydroxy-4-phosphonobutyl]purine yield=31%; lyophilizate; R$_f$=0.19 (iPrOH/H$_2$O/NH$_4$OH 7/2/1);

$^1$H NMR (D2O): δ=1.75-1.96 (m, 3H), 2.07-2.19 (m, 1H), 3.90-3.97 (m, 1H), 4.06-4.14 (m, 2H), 7.76 (s, 1H);

$^{31}$P NMR (DMSO-d6): 20.2;

MS (ESI) m/z 303.10 [M+H]+;

HRMS: calc. C9H16N6O4P [M+H]+ 303.0968, obs. 303.0971.

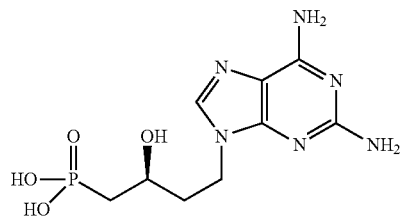 [SMILES: Nc1nc(N)c2ncn(CC[C@H](O)CP(=O)(O)O)c2n1]

2,6-diamino-9-[(2S)-2-hydroxy-4-phosphonobutyl]purine yield=70%; lyophilizate; R$_f$=0.20 (iPrOH/H$_2$O/NH$_4$OH 7/2/1);

$^1$H NMR (DMSO-d6): δ=1.73-1.98 (2m, 3H), 2.08-2.20 (m, 1H), 3.90-4.0 (m, 1H), 4.06-4.17 (m, 2H), 7.77 (s, 1H);

$^{31}$P NMR (DMSO-d6): 20.2;

MS (ESI) m/z 303.12 [M+H]+;

HRMS: calc. C9H16N6O4P [M+H]+ 303.0971, obs. 303.0971.

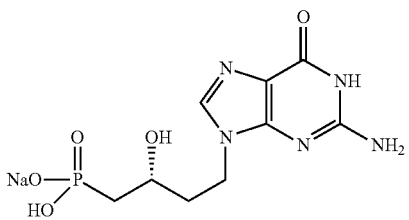

N-9-[(2R)-2-hydroxy-3-phosphonobutyl]guanine yield=68%; lyophilizate; R$_f$=0.60 (iPrOH/H$_2$O/NH$_4$OH 7/4/2);

[α]$^{20}_D$=+7 (c 0.0097, H2O);

$^1$H NMR (D2O): δ=1.77-1.96 (m, 3H), 2.08-2.21 (m, 1H), 3.87-3.98 (m, 1H), 4.05-4.17 (m, 2H), 7.75 (s, 1H);

$^{13}$C NMR (D2O): δ=35.4, 36.7, 37.0, 37.1, 40.6, 65.4, 115.7, 140.7, 151.3, 153.5, 158.7;

$^{31}$P NMR (D2O): δ=20.5;

MS (ESI) m/z 304.08 [M−Na+2H]$^+$, 326.06 [M+H]$^+$;

HRMS: calc. C9H15N5O5P [M+H]$^+$ 304.0811, obs. 304.0808.

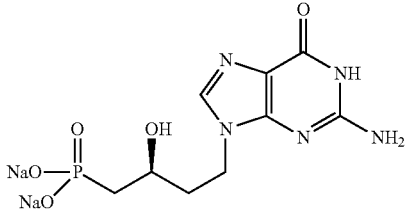

N-9-[(2S)-2-hydroxy-3-phosphono propyl]guanine yield=51%; lyophilizate; R$_f$=0.10 (iPrOH/H$_2$O/NH$_4$OH 7/2/1);

$^1$H NMR (D2O): δ=1.80-1.96 (m, 3H), 2.09-2.23 (m, 1H), 3.87-3.98 (m, 1H), 4.05-4.15 (m, 2H), 7.77 (s, 1H);

$^{13}$C NMR (D2O): δ=35.0, 36.8, 36.9, 37.0, 40.5, 65.2, 115.7, 140.0, 151.3, 153.5, 158.7;
$^{31}$P NMR (D2O): δ=21.0;
MS (ESI) m/z 348.04 [M+H]$^+$, 326.06 [M−Na+2H]$^+$, 304.08 [M−2Na+3H]$^+$;
HRMS: calc. C9H15N5O5P [M−2Na+3H]$^+$304.0811, obs. 304.0813.

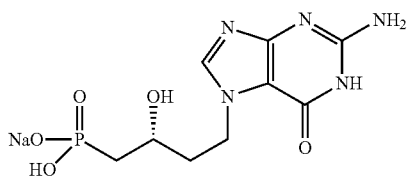

N-7-[(2R)-2-hydroxy-3-phosphonobutyl]guanine

Yield=34%; lyophilizate; R$_f$=0.22 (iPrOH/H$_2$O/NH$_4$OH 7/4/2); [α]$^{20}_D$=+2.2 (c 0.0104, H2O); $^1$H NMR (D2O): δ=1.80-1.90 (m, 3H), 2.02-2.21 (m, 1H), 3.92 (sl, 1H), 4.11-4.31 (m, 2H), 7.80 (s, 1H); $^{13}$C NMR (D2O): δ=35.3, 36.6, 38.0, 38.1, 43.9, 44.3, 54.1, 65.2, 65.4, 108.0, 144.0, 145.0, 153.1, 155.7, 158.3, 158.7, 159.3, 160.8; $^{31}$P NMR (D2O): δ=20.8; MS (ESI) m/z 302.07 [M−H]$^−$; 605.14 [2M−H]$^−$; HRMS: calc. C9H13N5O5P [M−H]$^−$ 302.0654, obs. 302.0657.

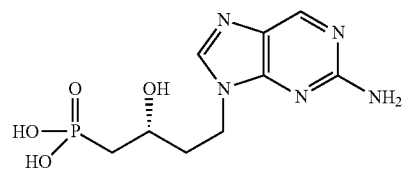 [SMILES: Nc1ncc2ncn(CC[C@@H](O)CP(=O)(O)O)c2n1]

N-9-[(2R)-2-hydroxy-3-phosphonobutyl] 2-aminopurine

Yield=40%; lyophilizate; R$_f$=0.32 (iPrOH/H$_2$O/NH$_4$OH 7/2/1); [α]$^{20}_D$=+2.8 (c 0.0124, H2O); $^1$H NMR (D2O): δ=1.85-2.11 (2m, 3H), 2.26-2.28 (m, 1H), 3.95-4.00 (m, 1H), 4.32 (m, 2H), 8.18 (s, 1H), 8.63-8.64 (d, 1H); $^{13}$C NMR (D2O): δ=35.3, 36.5, 36.6, 40.3, 65.3, 126.5, 145.2, 147.5, 152.9, 158.9; $^{31}$P NMR (D2O): δ=20.8; MS (ESI) m/z 286.07 [M−H]$^−$; 573.15 [2M−H]$^−$; HRMS: calc. C9H13N5O4P [M−H]$^−$ 286.0705, obs. 286.0704.

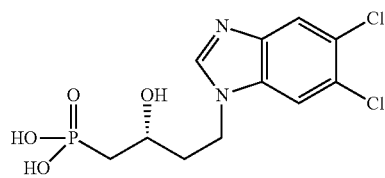 [SMILES: O=P(O)(O)C[C@H](O)CCn1cnc2cc(Cl)c(Cl)cc21]

N-1-[(2R)-2-hydroxy-4-phosphonobutyl] 5,6-dichlorobenzimidazole

Yield=34%; lyophilizate; R$_f$=0.53 (iPrOH/H$_2$O/NH$_4$OH 7/2/1); $^1$H NMR (D$_2$O): δ=1.75-1.98 (2m, 3H), 2.16-2.18 (m, 1H), 3.86 (m, 1H), 4.24-4.30 (m, 2H), 7.63 (bs, 2H), 8.14 (bs, 1H); $^{13}$C NMR (D$_2$O): δ=35.5, 36.7, 36.8, 41.9, 65.3, 112.1, 119.6, 125.7, 126.3; $^{31}$P NMR (D$_2$O): δ=20.7; MS (ESI) m/z 339.01 [M+H]$^+$; HRMS: calc. C$_{11}$H$_{14}$N$_2$O$_4$PCl$_2$ [M+H]$^+$ 339.0068, obs. 339.0070.

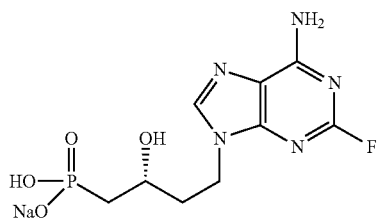

6-Amino-2-fluoro-9-[(2R)-2-hydroxy-4-phosphonobutyl]purine

Yield=26%; lyophilizate; R$_f$=0.39 (iPrOH/H$_2$O/NH$_4$OH 7/2/1); [α]$^{20}_D$=+3.5 (c 0.0071, H2O); $^1$H NMR (D$_2$O): δ=1.80-1.96 (m, 3H), 2.17-2.21 (m, 1H), 3.93-3.97 (m, 1H), 4.17 (t, 2H), 7.88 (s, 1H); $^{31}$P NMR (DMSO-d6): 20.7; $^{13}$C NMR (D$_2$O): δ=35.4, 36.7, 36.8, 40.3, 65.2, 141.5, 141.6, 150.8, 153.1, 157.2; MS (ESI) m/z 326.2 [M−H]$^−$.

The following compounds of formula (VIII) were synthesized:

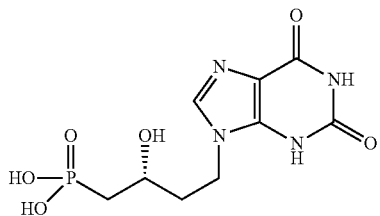 [SMILES: O=c1[nH]c(=O)c2ncn(CC[C@@H](O)CP(=O)(O)O)c2[nH]1]

N-9-[(2R)-2-hydroxy-4-phosphonobutyl]xanthine

Yield=46%; lyophilizate; R$_f$=0.17 (iPrOH/H$_2$O/NH$_4$OH 7/2/1); [α]$^{20}_D$=+17.5° (c 4.4, H2O); $^1$H NMR (D$_2$O): δ=1.84-2.00 (m, 3H), 2.20-2.27 (m, 1H), 3.94-4.00 (m, 1H), 4.21-4.24 (t, 2H), 7.79 (s, 1H); $^{13}$C NMR (D$_2$O): δ=35.9, 36.4, 41.6, 65.1, 115.2, 139.1, 143.2, 153.5, 160.0. $^{31}$P NMR (D$_2$O): 20.4; HRMS: calc. C$_9$H$_{14}$N$_4$O$_6$P [M−H]$^−$ 303.0494, obs. 303.0492.

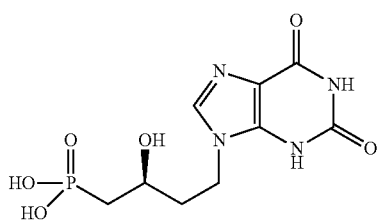 [SMILES: O=c1[nH]c(=O)c2ncn(CC[C@H](O)CP(=O)(O)O)c2[nH]1]

N-9-[(2S)-2-hydroxy-4-phosphonobutyl]xanthine

Yield=40%; lyophilizate; R$_f$=0.15 (iPrOH/H$_2$O/NH$_4$OH 7/2/1); [α]$^{20}_D$=−17.6° (c 4.9, H2O); $^1$H NMR (D$_2$O): δ=1.85-1.98 (m, 3H), 2.19-2.26 (m, 1H), 3.94-4.01 (m, 1H), 4.20-4.23 (t, 2H), 7.78 (s, 1H); $^{13}$C NMR (D$_2$O): δ=35.9, 36.5, 41.3, 65.1, 115.1, 139.2, 144.9, 154.5, 160.2. $^{31}$P NMR (D$_2$O): 20.4; HRMS: calc. C$_9$H$_{14}$N$_4$O$_6$P [M+H]$^+$ 305.0651, obs. 305.065.

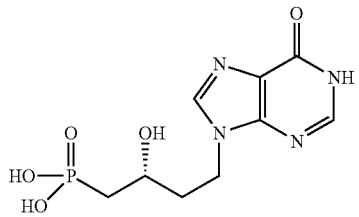 [SMILES: O=c1[nH]cnc2c1ncn2CC[C@@H](O)CP(=O)(O)O]

N-9-[(2R)-2-hydroxy-4-phosphonobutylhypoxanthine

Yield=70%; lyophilizate; R$_f$=0.19 (iPrOH/H$_2$O/NH$_4$OH 7/2/1); [α]$^{20}_D$=+16.3° (c 6.45, H2O); $^1$H NMR (D$_2$O): δ=1.76-1.81 (m, 2H), 1.99-2.03 (m, 1H), 2.20-2.28 (m, 1H), 3.93-4.00 (m, 1H), 4.37-4.40 (t, 2H), 8.16 (s, 1H), 8.19 (s, 1H); $^{13}$C NMR (D$_2$O): δ=35.9, 37.1, 41.3, 65.6, 123.3, 142.4, 145.5, 148.9, 158.7. $^{31}$P NMR (D$_2$O): 19.8; HRMS: calc. C$_9$H$_{12}$N$_4$O$_5$P [M−H]− 287.0545, obs. 287.0547.

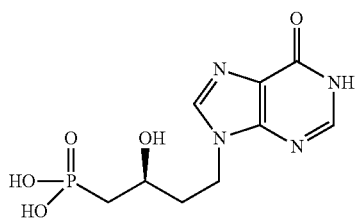 [SMILES: O=c1[nH]cnc2c1ncn2CC[C@H](O)CP(=O)(O)O]

N-9-[(2S)-2-hydroxy-4-phosphonobutyl]hypoxanthine

Yield=52%; lyophilizate; R$_f$=0.19 (iPrOH/H$_2$O/NH$_4$OH 7/2/1); [α]$^{20}_D$=−14.2° (c 4.7, H$_2$O); $^1$H NMR (D$_2$O): δ=1.81-1.86 (m, 2H), 1.99-2.04 (m, 1H), 2.24-2.30 (m, 1H), 3.92-3.99 (m, 1H), 4.38-4.41 (t, 2H), 8.16 (s, 1H), 8.19 (s, 1H). $^{13}$C NMR (D$_2$O): δ=36.0, 37.1, 41.3, 65.4, 123.3, 142.4, 145.5, 148.9, 158.7. $^{31}$P NMR (D$_2$O): 20.2; HRMS: calc. C$_9$H$_{14}$N$_4$O$_5$P [M+H]+ 289.0702, obs. 289.0703.

1.2.5 General Procedure for Synthesizing Compounds of Formula VI

A solution of trifluoroacetic acid (7/3, v/v) in dichloromethane (19 mL: 0.1 mmol) is added to a solution of the compound of formula IV (1 eq.) in anhydrous dichloromethane (1.5 mL: 0.1 mmol) under argon and at room temperature. The reaction medium is stirred at room temperature for 5 h, then concentrated at reduced pressure, and the residue is purified on a silica gel column (CH$_2$Cl$_2$/MeOH, 0-10%) leading, after evaporation of the pooled fractions, to the expected compound of formula VI.

The following compounds of formula (VI) were synthesized:

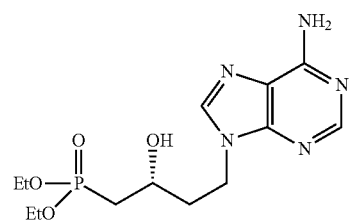 [SMILES: CCOP(=O)(C[C@H](O)CCn1cnc2c(N)ncnc21)OCC]

N-9-[(2R)-2-hydroxy-4-diethylphosphonobutyl] adenine

Yield=quantitative; white solid; R$_f$=0.42 (CH$_2$Cl$_2$/MeOH, 9/1, v/v); [α]$^{20}_D$=+15.0° (c 0.2, DCM); $^1$H NMR (CDCl$_3$): δ=1.27-1.31 (t, 6H), 1.88-2.02 (m, 3H), 2.10-2.18 (m, 1H), 3.81-3.93 (m, 1H), 4.04-4.12 (m, 4H), 4.33-4.49 (m, 2H), 6.87 (s, 2H), 7.91 (s, 1H), 8.31 (s, 1H); 31P NMR (CDCl$_3$): 28.7; $^{13}$C NMR (CDCl$_3$): δ=16.4, 16.5, 33.6, 38.2, 40.9, 62.1, 62.3, 63.2, 119.5, 142.0, 149.9, 150.3, 154.5; HRMS: calc. C$_{13}$H$_{23}$N$_5$O$_4$P [M+H]$^+$ 344.1488, obs. 344.1487.

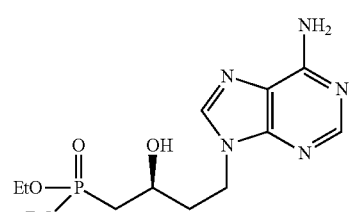

N-9-[(2S)-2-hydroxy-4-diethylphosphonobutyl] adenine

Yield=quantitative; white solid; R$_f$=0.39 (CH$_2$Cl$_2$/MeOH, 9/1, v/v); [α]$^{20}_D$=−16.2° (c 0.1, DCM); $^1$H NMR (CDCl$_3$): δ=1.27-1.31 (2t, 6H), 1.85-2.20 (m, 3H), 3.79-3.96 (m, 1H), 4.0-4.17 (m, 4H), 4.31-4.50 (m, 2H), 6.87 (s, 2H), 7.91 (s, 1H), 8.31 (s, 1H); 31P NMR (CDCl$_3$): 28.7; $^{13}$C NMR (CDCl$_3$): δ=16.4, 16.5, 33.5, 38.2, 40.9, 62.2, 62.3, 63.2, 119.5, 142.0, 149.9, 150.3, 154.5; HRMS: calc. C$_{13}$H$_{23}$N$_5$O$_4$P [M+H]$^+$ 344.1488, obs. 344.1490.

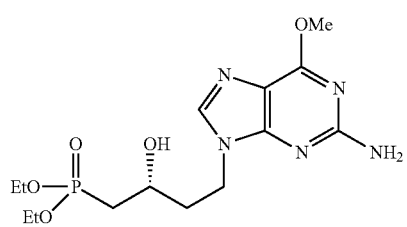 [SMILES: CCOP(=O)(C[C@H](O)CCn1cnc2c(OC)nc(N)nc21)OCC]

N-9-[(2R)-2-hydroxy-4-diethylphosphonobutyl] 2-amino-6-O-methylpurine

Yield=quantitative; white solid; R$_f$=0.50 (CH$_2$Cl$_2$/MeOH, 9/1, v/v); [α]$^{20}_D$=+20.9° (c 0.5, DCM); $^1$H NMR (CDCl$_3$): δ=1.28-1.32 (2t, 6H), 1.88-2.14 (m, 4H), 3.91-4.01 (m, 1H), 4.03-4.12 (m, 4H), 4.13 (s, 3H), 4.26-4.43 (m, 2H), 7.81 (s, 1H); 31P NMR (CDCl$_3$): 29.1; $^{13}$C NMR (CDCl$_3$): δ=16.4, 16.5, 33.4, 38.1, 41.4, 54.1, 62.3, 62.4, 63.4, 114.7, 140.2, 149.3, 157.8, 162.2; HRMS: calc. $C_{14}H_{25}N_5O_5P$ $[M+H]^+$ 374.1593, obs. 374.1589.

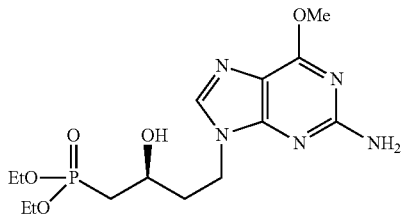

N-9-[(2S)-2-hydroxy-4-diethylphosphonobutyl] 2-amino-6-O-methylpurine

Yield=quantitative; white solid; $R_f$=0.50 ($CH_2Cl_2$/MeOH, 9/1, v/v); $[\alpha]^{20}_D$=−17.6° (c 1.0, DCM); $^1$H NMR ($CDCl_3$): δ=1.28-1.32 (2t, 6H), 1.92-2.13 (m, 4H), 3.90-4.02 (m, 1H), 4.05-4.12 (m, 4H), 4.13 (s, 3H), 4.25-4.42 (m, 2H), 7.81 (s, 1H); 31P NMR ($CDCl_3$): 29.2; $^{13}$C NMR ($CDCl_3$): δ=16.4, 16.5, 33.8, 38.1, 41.4, 55.1, 62.3, 62.4, 63.4, 114.7, 140.2, 149.3, 157.8, 162.2; HRMS: calc. $C_{14}H_{25}N_5O_5P$ $[M+H]^+$ 374.1593, obs. 374.1597.

An aqueous solution of sodium nitrite (15 eq., 2.22 mL: 1 mmol of $NaNO_2$) is added dropwise to a solution of the compound of formula VI (1 eq.) in acetic acid 1M (15 mL: 1 mmol) heated to 65° C. The reaction medium is stirred at 65° C. for 2 h, then cooled in an ice bath and neutralized to pH 7 by the addition of an aqueous sodium hydroxide solution 1M. The reaction medium is then concentrated at reduced pressure, and the residue is purified by reverse phase chromatography on a silica gel column ($H_2O$/MeOH, 0-100%) leading, after evaporation of the pooled fractions and lyophilization of the residue, to the expected compound of formula VII.

The following compounds of formula (VII) were synthesized:

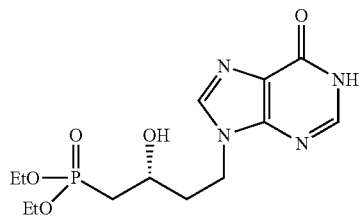

N-9-[(2R)-2-hydroxy-4-diethylphosphonobutyl] hypoxanthine

Yield=66%; white solid; $R_f$=0.3 ($CH_2Cl_2$/MeOH, 9/1, v/v); $[\alpha]^{20}_D$=+14.8° (c 1.2, DCM); $^1$H NMR ($CDCl_3$): δ=1.27-1.31 (2t, 6H), 1.93-2.18 (m, 4H), 3.90-3.97 (m, 1H), 4.08-4.12 (m, 4H), 4.30-4.44 (m, 2H), 7.91 (s, 1H), 8.14 (s, 1H); 31P NMR ($CDCl_3$): 29.4; $^{13}$C NMR ($CDCl_3$): δ=16.5, 16.6, 33.8, 38.4, 40.9, 62.1, 62.3, 63.2, 124.7, 140.9, 145.3, 149.2, 159.2; HRMS: calc. $C_{13}H_{22}N_4O_5P$ $[M+H]^+$ 345.1328, obs. 345.1326.

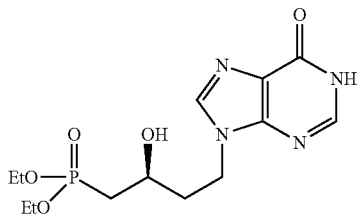

N-9-[(2S)-2-hydroxy-4-diethylphosphonobutyl] hypoxanthine

Yield=83%; white solid; $R_f$=0.32 ($CH_2Cl_2$/MeOH, 9/1, v/v); $[\alpha]^{20}_D$=−16.5° (c 0.5, DCM); $^1$H NMR ($CDCl_3$): δ=1.23 (t, 6H), 2.00-2.08 (m, 1H), 2.14-2.29 (m, 3H), 3.80-3.85 (m, 1H), 4.01-4.08 (m, 4H), 4.40-4.44 (m, 2H), 8.14 (s, 1H), 8.22 (s, 1H); 31P NMR ($D_2O$): 31.0; $^{13}$C NMR ($D_2O$): δ=15.4, 15.5, 32.5, 36.9, 40.9, 63.2, 63.3, 63.4, 142.3, 146.1; HRMS: calc. $C_{13}H_{22}N_4O_5P$ $[M+H]^+$ 345.1328, obs. 345.1329.

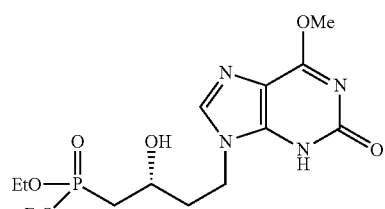

N-9-[(2R)-2-hydroxy-4-diethylphosphonobutyl] 6-O-methyl-2-oxopurine

Yield=49%; white solid; $R_f$=0.40 ($CH_2Cl_2$/MeOH, 9/1, v/v); $[\alpha]^{20}_D$=+19.6° (c 0.6, DCM); $^1$H NMR ($D_2O$): δ=1.17-1.21 (2t, 6H), 1.9-2.00-2.08 (m, 1H), 2.11-2.25 (m, 3H), 3.66-3.84 (m, 1H), 3.97-4.07 (m, 4H), 4.04 (s, 3H), 4.21-4.24 (m, 2H), 7.79 (s, 1H); 31P NMR ($D_2O$): 31.2; $^{13}$C NMR ($D_2O$): δ=15.3, 15.45, 32.3, 37.0, 39.8, 53.8, 63.1, 63.2, 63.3, 112.4, 140.1, 154.3, 162.0, 166.8; HRMS: calc. $C_{14}H_{24}N_4O_6P$ $[M+H]^+$ 375.1433, obs. 375.1431.

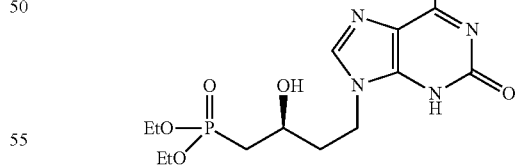

N-9-[(2S)-2-hydroxy-4-diethylphosphonobutyl] 6-O-methyl-2-oxopurine

Yield=53%; white solid; $R_f$=0.41 ($CH_2Cl_2$/MeOH, 9/1, v/v); $[\alpha]^{20}_D$=−20.2° (c 1.1, DCM); $^1$H NMR ($D_2O$): δ=1.17-1.21 (2t, 6H), 1.9-2.00-2.08 (m, 1H), 2.11-2.24 (m, 3H), 3.66-3.84 (m, 1H), 3.97-4.06 (m, 4H), 4.04 (s, 3H), 4.21-4.24 (m, 2H), 7.79 (s, 1H); 31P NMR ($D_2O$): 31.2; $^{13}$C NMR ($D_2O$): δ=15.3, 15.4, 32.3, 36.9, 39.8, 53.8, 63.1, 63.2, 63.3, 112.4, 140.1, 154.4, 162.0, 166.9; HRMS: calc. $C_{14}H_{24}N_4O_6P$ [M+H]+ 375.1433, obs. 375.1434.

1.2.7 General Procedure for Synthesizing the Prodrugs: Compounds of Formula X

The general procedure for synthesizing the prodrugs is illustrated in diagram 3 below

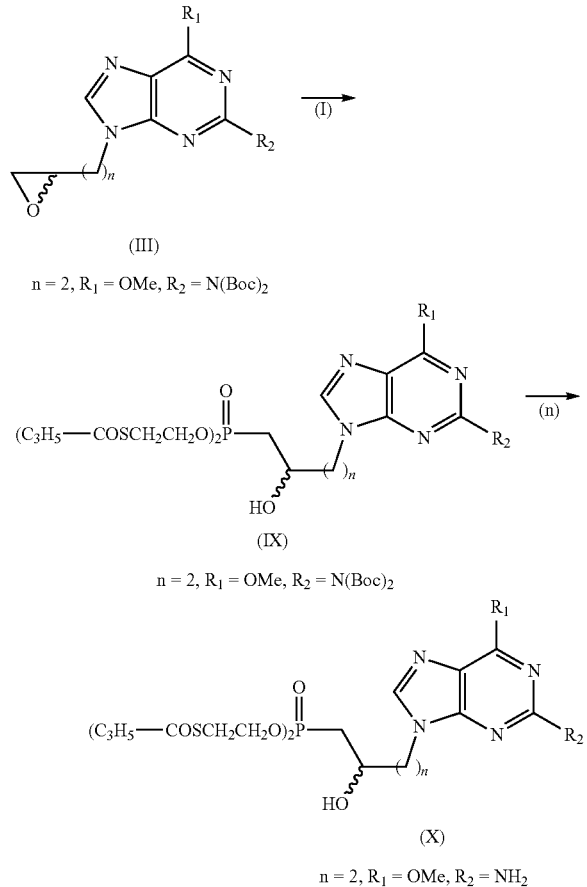

(i) 1) HP(O)(OPheSATE)$_2$, N,O-BSA, dichloromethane, reflux, 3 h,
2) Compound III, BF$_3$·OEt$_2$, CH$_2$Cl$_2$, −60° C., 3 h, rt, 16 h; (ii) CF3COOH, dichloromethane, 0° C., 30 min, then, rt, 3 h.

The N,O—BSA (6.5 eq.) is added to a solution of bis(S-benzoyl-2-thioethyl)phosphite [HP(O)(OPheSATE)$_2$] prepared according to the method described by A. Hospital et al. (Org. Lett. 2013, 15, 18, 4778-81) and A. D. Briggs et al. (Eur. J. Pharm. Sci., 1997, 5, 199) (6 eq.) in anhydrous dichloromethane (1 mL/mmol) and under argon. The reaction medium is heated at reflux for 3 h, then cooled to room temperature, then to −60° C. A solution of compound III (1 eq.) in anhydrous dichloromethane is transferred by cannula to the preceding reaction medium, then a solution of BF$_3$.OEt$_2$ (6 eq.) is added. The reaction medium is maintained under stirring at −60° C. for 3 h, then left at room temperature. After stirring overnight, the reaction medium is concentrated at reduced pressure. The residue is purified on a silica gel column (AcOEt/Acetone, 0-50%) leading, after evaporation of the pooled fractions, to the expected compound (formula IX).

The following compounds of formula (IX) were synthesized:

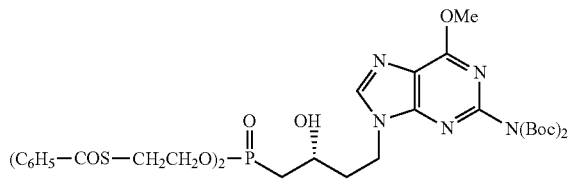

N$^2$,N$^2$-Bis(tert-butoxycarbonyl)-6-O-methyl-9-[(2R)-2-hydroxy-4-bis(S-benzoyl-2-thioethyl)phosphonobutyl]-2-aminopurine yield=23%; oil;

$[\alpha]^{20}_D$=+6.9 (c 0.0101, HCCl3); $R_f$=0.4 (CH$_2$Cl$_2$/MeOH, 95/5, v/v);

$^1$H NMR (CDCl$_3$): δ=1.43 (s, 18H), 2.15 (s, 2H), 2.61 (m, 2H), 3.30 (t, 4H), 4.0-4.39 (m, 9H), 7.42 (m, 4H), 7.55 (m, 2H), 7.88-8.0 (m, 5H);

$^{31}$P NMR (CDCl$_3$): 29.9;

$^{13}$C NMR (CDCl$_3$): δ=27.8, 29.2, 29.7, 30.3, 31.7, 31.9, 40.6, 53.9, 54.5, 63.0, 64.4, 64.3, 83.2, 127.3, 128.7, 133.7, 136.5, 151.0, 190.9;

MS (ESI) m/z 846.26 [M+H]+, 746.21 [M-Boc+2H]+; 646.16 [M-2Boc+3H]+.

N$^2$,N$^2$-Bis(tert-butoxycarbonyl)-6-O-methyl-9-[(2S)-2-hydroxy-4-bis(S-benzoyl-2-thioethyl)phosphonobutyl]-2-aminopurine yield=23%; oil; $R_f$=0.7 (CH$_2$Cl$_2$/MeOH, 9/1, v/v);

$^1$H NMR (CDCl$_3$): δ=1.39 (s, 18H), 1.93-2.05 (m, 4H), 3.26 (pt, 4H), 3.81 (m, 1H), 4.06 (s, 3H), 4.15-4.49 (2m, 6H), 7.38 (pt, 4H), 7.50 (pt, 2H), 7.87 (m, 5H);

$^{31}$P NMR (CDCl$_3$): 29.8;

$^{13}$C NMR (CDCl$_3$): δ=28.0, 29.4, 29.9, 32.1, 33.2, 34.6, 41.2, 54.9, 63.2, 64.4, 64.5, 83.5, 127.5, 128.9, 133.9, 136.7, 143.3, 151.0, 190.9;

MS (ESI) m/z 846.26 [M+H]+, 746.21 [M-Boc+2H]+; 646.16 [M-2Boc+3H]+.

A solution of trifluoroacetic acid in anhydrous dichloromethane (1.3 mL, 1/1, v/v) is added to a solution of the compound of formula IX (1 eq.), obtained according to the example above, in anhydrous dichloromethane (10 mL/mmol) cooled to 0° C., and under argon. The reaction medium is stirred at 0° C. for 30 min, then allowed to return to room temperature. After 2 h 30, the reaction medium is diluted with absolute ethanol, then concentrated at reduced pressure. The residue is purified on a silica gel column (DCM/MeOH, 0-10%) leading, after evaporation of the pooled fractions, to the expected compound (formula X).

The following compounds of formula (X) were synthesized:

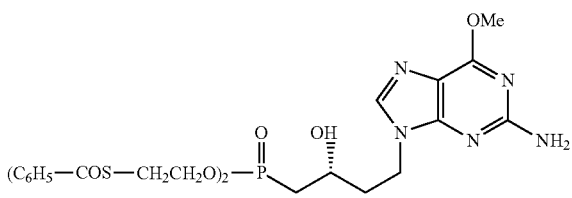

6-O-methyl-9-[(2R)-2-hydroxy-4-bis(S-benzoyl-2-thioethyl)phosphonobutyl]-2-aminopurine yield=53%; oil;

$[\alpha]^{20}_D$=+16.7 (c 0.0078, HCCl3); $R_f$=0.27 (CH$_2$Cl$_2$/MeOH, 95/5, v/v);

$^1$H NMR (CDCl$_3$): δ=1.95 (m, 4H), 3.27 (pt, 4H), 3.86 (m, 1H), 3.98 (s, 3H), 4.08-4.40 (m, 6H), 7.40 (m, 4H), 7.57 (m, 3H), 7.85 (m, 4H);

$^{31}$P NMR (CDCl$_3$): 30.1;

$^{13}$C NMR (CDCl$_3$): δ=28.2, 31.6, 33.4, 37.3, 37.5, 39.4, 53.3, 61.9, 63.2, 113.7, 126.3, 127.7, 132.7, 135.5, 138.7, 151.2, 157.8, 160.9, 189.8, 190.0;

MS (ESI) m/z 646.17 [M+H]+.

HRMS: calc. C28H33N5O7PS2 [M+H]+ calc. 646.1559, obs. 646.1560.

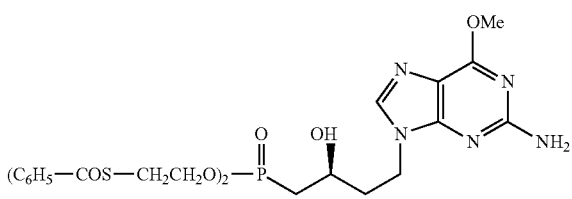

6-O-methyl-9-[(2S)-2-hydroxy-4-bis(S-benzoyl-2-thioethyl)phosphonobutyl]-2-amino Purine yield=97%; oil; $R_f$=0.23 (CH$_2$Cl$_2$/MeOH, 95/5, v/v);

$^1$H NMR (CDCl$_3$): δ=1.75-2.20 (m, 3H), 2.26 (m, 1H), 3.23 (m, 4H), 3.85-4.10 (m, 4H), 4.17 (m, 5H), 7.33 (m, 4H), 7.47 (m, 2H), 7.59 (s, 1H), 7.72-7.81 (m, 4H); 31P NMR (CDCl$_3$): 30.4;

$^{13}$C NMR (CDCl$_3$): δ=28.0, 28.2, 30.3, 35.4, 37.3, 37.5, 39.1, 52.5, 53.1, 61.9, 63.8, 113.2, 114.0, 116.8, 126.2, 127.4, 132.7, 135.4, 138.4, 151.7, 158.3, 160.7, 161.6, 161.9, 189.7, 199.8;

MS (ESI) m/z 646.16 [M+H]+;

HRMS: calc. C28H33N5O7PS2 [M+H]+ calc. 646.1559, obs. 646.1563.

Example 2: Detection of the Anti-Parasitic Activity and of the Toxicity of the Compounds The structure of the different compounds tested is presented in table 1 below:

TABLE 1 structure of the compounds tested

| Number of the compound | A | n | Y | Configuration of C* | $R_6$ |
|---|---|---|---|---|---|
| 1 | Adenine | 1 | —OH | S | —H |
| 2 | Adenine | 1 | —OH | R | —H |
| 3 | Guanine | 1 | —OH | S | —H |
| 4 | Guanine | 1 | —OH | S | PheSATE |
| 5 | Guanine | 1 | —OH | R | —H |
| 6 | Guanine | 1 | —OH | R | PheSATE |
| 7 | 2,6-Diaminopurine | 1 | —OH | S | —H |
| 8 | 2,6-Diaminopurine | 1 | —OH | R | —H |
| 9 | Adenine | 0 | —OH | S | —H |
| 10 | Adenine | 0 | —OH | R | —H |
| 11 | Guanine | 0 | —OH | R | —H |
| 12 | Guanine | 0 | —OH | S | —H |
| 13 | 2,6 Diaminopurine | 0 | —OH | R | —H |
| 14 | 2,6 Diaminopurine | 0 | —OH | S | —H |
| 15 | 6-Amino,2-fluoropurine | 1 | —OH | R | —H |
| 16 | 2-Aminopurine | 1 | —OH | R | —H |
| 17 | N-7-Guanine | 1 | —OH | R | —H |
| 18 | 5,6-Dichlorobenzimidazole | 1 | —OH | R | —H |
| 19 | 2,6 Oxopurine | 1 | —OH | R | —H |
| 20 | 6 Oxopurine | 1 | —OH | R | —H |
| 21 | 6 Oxopurine | 1 | —OH | S | —H |
| 22 | 2,6 Oxopurine | 1 | —OH | S | —H |

2.1. Detection of the In Vitro Anti-*Plasmodium falciparum* Activity

The measurement of the anti-malarial activity consists in bringing the erythrocytes infected with by *Plasmodium falciparum* (strain 3D7) in contact with variable concentrations of the compound to be tested for 48 h (or the duration of one cycle of *P. falciparum*). The culturing conditions are 1.5% of hematocrit and 0.6% of initial parasitemia in complete medium (RPMI 1640+10% human serum AB$^+$+ gentamycin). The viability of the parasite is measured by its ability to synthesize the nucleic acids from a radioactive precursor, [$^3$H]-hypoxanthine or $^3$H-ethanolamine.

After 48 h of incubation in the absence (control) or in the presence of the compound to be tested, the radioactive precursor is added, and the reaction is continued for another 18 h, then stopped by freezing at −80° C. The macromolecules, including the radiolabeled nucleic acids, are collected on a filter. The incorporated radioactivity is measured with the scintillation counter after addition of scintillation cocktail.

The radioactive background noise is measured based on a suspension of healthy erythrocytes (same conditions as for parasite-containing suspensions). The viability of the parasites is expressed as a (nonspecific derived) percentage of the control. The measurements are analyzed by means of the Excel and Prism software and the IC$_{50}$ (concentration capable of in vitro inhibition of 50% of the growth of the parasites) is determined graphically.

The IC$_{50}$ values thus determined are the result of at least two experiments carried out independently in duplicate. The results obtained are detailed in Table 2 below. Batches A and B correspond to two different syntheses according to the same procedure and carried out in their totality by two different operators, at a six month interval.

TABLE 2

Experimental results

| Compound Ref. | Activity against *P. falciparum* (3D7) Detection | | | | Activity against the K562 cells |
|---|---|---|---|---|---|
| | ³H- | | | | |
| | ³H-Hypoxanthine Batch A IC$_{50}$ (µM) | ³H-Hypoxanthine Batch B IC$_{50}$ (µM) | Ethanolamine Batch A IC$_{50}$ (µM) | ³H-Thymidine Batch B IC$_{50}$ (µM) | |
| 1 | >1000 | Nd | >1000 | Nd | |
| 2 | >1000 | Nd | >1000 | Nd | |
| 3 | 3.3 | 7.05 | 6 | >5,000 | |
| 4 | Nd | 57 | Nd | 22 | |
| 5 | 0.058 | 0.0775 | 0.043 | 10,000 | |
| 6 | Nd | 62 | Nd | 20 | |
| 7 | ≥1000 | Nd | >1000 | Nd | |
| 8 | 48 | Nd | 120 | Nd | |
| 9 | >1000 | Nd | >1000 | Nd | |
| 10 | >1000 | Nd | >1000 | Nd | |
| 11 | ≥1000 | Nd | >1000 | Nd | |
| 12 | Nd | Nd | Nd | Nd | |
| 13 | 510 | Nd | 740 | Nd | |
| 14 | 595 | Nd | 650 | Nd | |
| 15 | 26 | | | | |
| 16 | 62 | | | | |
| 18 | >100 | | | | |
| 19 | >100 | | | | |
| 20 | >1000 | | | | |
| 21 | >1000 | | | | |
| 22 | 910 | | | | |
| Chloroquine | 0.0145 | Nd | 0.014 | Nd | |

Nd: not determined 2.2. Detection of the Toxicity of Compounds with Respect to K562 Cells Suspensions of human cells (8000 cells per well) are cultured in complete RPMI medium (RPMI 1640 medium, L-glutamine, penicillin/streptomycin and 10% fetal calf serum) (200 µL) either in the absence of the compound to be tested (controls), or in contact with variable concentrations of said compound.

After 24 h of incubation (or approximately one cell cycle), 0.7 µCi of [³H]-thymidine (radiolabeled precursor of the synthesis of the nucleic acids) diluted in 30 µL of complete RPMI medium are added to each well. After 6 h of additional incubation, the thymidine incorporation reaction is stopped by freezing at −80° C. As for the determination of the in vitro anti-malarial activity, the macromolecules, including the radiolabeled nucleic acids, are collected on a filter. The incorporated radioactivity is measured with the scintillation counter after addition of scintillation cocktail.

The radioactive background noise is measured based on complete RPMI medium. The viability of the cells is expressed as a (nonspecific derived) percentage of the control. The measurements are analyzed using Excel and Prism software, and the IC$_{50}$ (concentration capable of in vitro inhibition of 50% of the growth of the cells) is determined graphically.

The IC$_{50}$ values thus determined are the result of at least two experiments performed independently in duplicate.

The results obtained are detailed in Table 2 above.

2.2. Detection of the In Vitro Anti-*Babesia divergens* Activity

The activity of compounds against the growth of the *Babesia divergens* is measured by bringing the erythrocytes infected with *Babesia divergens* in contact with variable concentrations of compound to be tested for 16 h (that is to say the duration of 2 cycles of *B. divergens*). The culturing conditions are 1.5% of hematocrit and 0.6% of initial parasitemia in the complete medium (RPMI 1640+10% human serum AB⁺+gentamycin). The viability of the parasite is measured by its ability to synthesize the nucleic acids from a radioactive precursor, [³H]-hypoxanthine.

After 16 h of incubation in the absence (control) or in the presence of the compound, the radioactive precursor is added and the reaction is continued for another 8 h and then stopped by freezing at −80° C. As for the determination of the in vitro anti-parasitic activity, the macromolecules, including the radiolabeled nucleic acids, are collected on a filter. The incorporated radioactivity is measured with the scintillation counter after addition of scintillation cocktail.

The radioactive background noise is measured based on a suspension of healthy erythrocytes (same conditions as for the parasite-containing suspensions). The viability of the parasites is expressed as a (nonspecific derived) percentage of the control. The measurements are analyzed using Excel and Prism software, and the IC$_{50}$ (concentration capable of in vitro inhibition of 50% of the growth of the cells) is determined graphically.

The IC$_{50}$ values thus determined are the result of at least two experiments performed independently in duplicate. The results obtained are detailed in Table 3 below.

TABLE 3 experimental results

| Compound Ref. | Activity against *Babesia divergens* IC$_{50}$ (µM) |
|---|---|
| 3 | 3.6 |
| 5 | 0.48 |
| 12 | >1000 |
| 15 | 185 |
| 16 | >100 |
| 18 | 470 |
| 19 | >100 |
| 20 | >100 |
| 21 | >100 |
| 22 | >1000 |
| Pentamidine | 0.183 |

2.3. Detection of the In Vitro Anti-Toxoplasmosis Activity by "Plaque Assay"

This test is based on the capability of *Toxoplasma gondii* in its intracellular form (tachyzoite) to bring about the lysis of its host cell (here a monolayer of fibroblasts) and to then infect the neighboring cells so that over time (days) a macroscopically visible hole in the monolayer of cells becomes apparent and its area can be measured. In the 24-well culturing plates, approximately 80 parasites are added to a monolayer of fibroblasts (HFF cells) for 7 days in the presence or absence of drug. The cells are then fixed with 4% paraformaldehyde, and then stained with Giemsa. The cells are visualized under the microscope, and the size of the lysis plaques is measured using the software Zen® (Zeiss). The cells are maintained in culture in complete medium (DMEM+5% fetal calf serum+glutamine+penicillin/streptomycin). The ability of the drug to inhibit the growth of *Toxoplasma gondii* is proportional to the decrease in the size of the lysis plaque.

The results obtained are collected in Table 4 (average of 2 values) below and in FIG. 1.

TABLE 4

| | experimental results | |
|---|---|---|
| | Inhibition of the growth of *T. gondii* (% of the controls) | |
| Compound Ref. | Conc = 5 µM | Conc = 50 µM |
| 3 | 0 | 18 |
| 5 | 42 | 100 |
| 15 | 18 | 7 |

The invention claimed is:

1. A method for treatment of an infection caused by an organism auxotrophic for purines, said organism being selected from bacteria and protozoans,
   wherein said infection is caused by an agent selected from: *Plasmodium falciparum, Plasmodium vivax, Plasmodium malariae, Plasmodium ovale, Plasmodium knowlesi, Giardia lamblia, Helicobacter pylori, Mycobacterium tuberculosis, Escherichia coli, Trypanosoma brucei, Babesia divergens, Babesia canis* and *Toxoplasma gondii*, and
   wherein said method comprises administering to a subject in need thereof a compound having the following general formula (I):

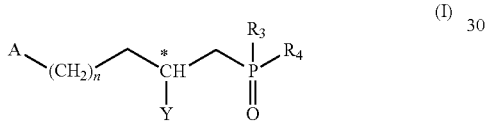

(I)

in which
   A represents a heterocycle of formula (IIA) or a heterocycle of formula (IIB), as below:

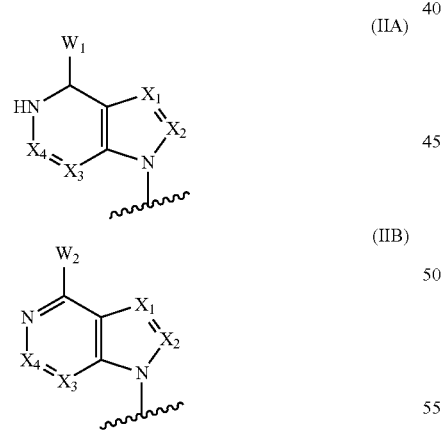

in which:
   $W_1$ represents an oxygen atom or a sulfur atom;
   $W_2$ represents a halogen atom, a —$OR_5$ group, a —$SR_5$ group, a —$NHR_5$ group or a —$N(R_5)_2$ group;
   $X_1$ represents a nitrogen atom or a —CH— group;
   $X_2$ represents a nitrogen atom, a —$CR_1$ group or a —C=O group;
   $X_3$ represents a nitrogen atom or a —CH— group;
   $X_4$ represents a nitrogen atom, a —$CR_2$ group or a —C=O group;

$R_1$ represents:
   a hydrogen atom, or
   a halogen atom, or
   a group selected from:
      a —$NHR_5$ group,
      a —$N(R_5)_2$ group,
      a —$OR_5$ group,
      a —$SR_5$ group,
      a $C_1$-$C_6$ alkyl group,
      an aryl group,
      a heteroaryl group;
$R_2$ represents:
   a hydrogen atom, or
   a halogen atom, or
   a group selected from:
      a —$NHR_5$ group,
      a —$N(R_5)_2$ group,
      a —$OR_5$ group,
      a $C_1$-$C_6$ alkyl group,
      an aryl group,
      a heteroaryl group;
      a $C_2$-$C_6$ alkenyl group,
      a $C_2$-$C_6$ alkynyl group,
      an aryl ($C_1$-$C_6$) alkyl group,
      a ($C_1$-$C_6$) alkylaryl group,
      a heteroaryl($C_1$-$C_6$)alkyl group;
$R_3$ and $R_4$, which are identical or different, each represent, independently of one another:
      a —$OR_6$ group, or
      a —$NHR_7$ group, or
      a —$N(R_7)_2$ group;
$R_5$ represents:
   a hydrogen atom
   a $C_1$-$C_6$ alkyl group,
   a $C_2$-$C_6$ alkenyl group,
   a $C_2$-$C_6$ alkynyl group,
   an aryl group,
   a $C_1$-$C_6$ acyl group,
   an aryl($C_1$-$C_6$)alkyl group,
   said groups optionally containing one or more heteroatoms;
$R_6$ represents:
   a hydrogen atom, a sodium atom or a lithium atom, or
   a group selected from:
      an ammonium group,
      a —$N(R_aR_bR_cR_d)^+$ group with $R_a$, $R_b$, $R_c$ and $R_d$, which are identical or different, each representing a hydrogen atom or a $C_1$-$C_4$ alkyl group,
      an aryl group,
      a S—($C_1$-$C_{12}$)alkyl-2-dithioethyl group, said alkyl group optionally including at least one heteroatom,
      a S—($C_1$-$C_{12}$)aryl-2-dithioethyl group, said aryl group optionally including at least one heteroatom,
      a S—($C_1$-$C_6$)acyl-2-thioethyl group, said acyl group optionally including at least one heteroatom,
      a ($C_1$-$C_6$)alkyloxy($C_1C_6$)alkyl ester group,
      an alkoxy($C_1$-$C_6$)carbonyloxymethyl ester group,
      a $C_{12}$-$C_{20}$ alkyl group optionally including at least one heteroatom,
$R_7$ represents:
   a $C_1$-$C_6$ alkyl chain,
   an aryl group, or
   an amino acid residue, an amino acid ester derivative or an amino acid amide derivative;

n is a whole number equal to 0, 1 or 2;
Y represents a substituent selected from: a halogen atom, a —$OR_5$ group, a —$SR_5$ group, a —$NHR_5$ group and a —$N(R_5)_2$ group;
C* represents a chiral carbon atom,
or a stereoisomer or pharmaceutically acceptable salt thereof.

2. The method according to claim 1, in which in formula (I) A represents a purine selected from: guanine, xanthine, hypoxanthine, adenine, 2-aminopurine and 2,6-diaminopurine.

3. The method according to claim 2, wherein in formula (I):
A represents guanine;
n is equal to 1;
Y represents a hydroxyl group;
the chiral carbon C* has configuration R, and
$R_3$ and $R_4$ each represent an —$OR_6$ group in which $R_6$ is a sodium atom.

4. The method according to claim 1 wherein said infection is an infection caused by *Plasmodium falciparum*.

5. A compound having the following general formula (I):

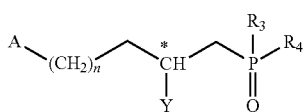

in which
A represents a heterocycle having formula (IIA) as below:

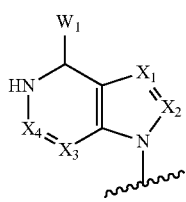

in which:
$W_1$ represents an oxygen atom or a sulfur atom;
$X_1$ represents a nitrogen atom or a —CH— group;
$X_2$ represents a nitrogen atom, a —$CR_1$ group or a —C=O group;
$X_3$ represents a nitrogen atom or a —CH— group;
$X_4$ represents a nitrogen atom, a —$CR_2$ group or a —C=O group;
$R_1$ represents:
a hydrogen atom, or
a halogen atom, or
a group selected from:
a —$NHR_5$ group,
a —$N(R_5)_2$ group,
a —$OR_5$ group,
a —$SR_5$ group,
a $C_1$-$C_6$ alkyl group,
an aryl group,
a heteroaryl group;
$R_2$ represents:
a hydrogen atom, or
a halogen atom, or
a group selected from:
a —$NHR_5$ group,
a —$N(R_5)_2$ group,
a —$OR_5$ group,
a $C_1$-$C_6$ alkyl group,
an aryl group,
a heteroaryl group;
a $C_2$-$C_6$ alkenyl group,
a $C_2$-$C_6$ alkynyl group,
an aryl ($C_1$-$C_6$)alkyl group,
a ($C_1$-$C_6$)alkylaryl group,
a heteroaryl($C_1$-$C_6$)alkyl group;
$R_3$ and $R_4$, which are identical or different, each represent, independently of one another:
a —$OR_6$ group, or
a —$NHR_7$ group, or
a —$N(R_7)_2$ group;
$R_5$ represents:
a hydrogen atom
a $C_1$-$C_6$ alkyl group,
a $C_2$-$C_6$ alkenyl group,
a $C_2$-$C_6$ alkynyl group,
an aryl group,
a $C_1$-$C_6$ acyl group,
an aryl($C_1$-$C_6$)alkyl group,
said groups optionally containing one or more heteroatoms;
$R_6$ represents:
a hydrogen atom, a sodium atom or a lithium atom, or
a group selected from:
an ammonium group
a —$N(R_aR_bR_cR_d)^+$ group with $R_a$, $R_b$, $R_c$ and $R_d$, which are identical or different, each representing a hydrogen atom or a $C_1$-$C_4$ alkyl group,
an aryl group,
a S—($C_1$-$C_{12}$)alkyl-2-dithioethyl group, said alkyl group optionally including at least one heteroatom,
a S—($C_1$-$C_{12}$)aryl-2-dithioethyl group, said aryl group optionally including at least one heteroatom,
a S—($C_1$-$C_6$)acyl-2-thioethyl group, said acyl group optionally including at least one heteroatom,
a ($C_1$-$C_6$)alkyloxy($C_1C_6$)alkyl ester group,
an alkoxy($C_1$-$C_6$)carbonyloxymethyl ester group,
a $C_{12}$-$C_{20}$ alkyl group optionally including at least one heteroatom,
$R_7$ represents:
a $C_1$-$C_6$ alkyl chain,
an aryl group, or
an amino acid residue, an amino acid ester derivative or an amino acid amide derivative;
n is a whole number equal to 0, 1 or 2;
Y represents a substituent selected from: a chlorine atom, bromine atom, iodine atom, a —$OR_5$ group, a —$SR_5$ group, a —$NHR_5$ group and a —$N(R_5)_2$ group;
C* represents a chiral carbon atom.

6. The compound according to claim 5, wherein:
$W_1$ represents an oxygen atom;
$X_1$ represents a nitrogen atom;
$X_2$ represents a —$CR_1$ group, $R_1$ representing a hydrogen atom;
$X_3$ represents a nitrogen atom;

$X_4$ represents a —$CR_2$ group with $R_2$ representing a —$NH_2$ group;

n is equal to 1;

Y represents a hydroxyl group;

the chiral carbon C* has configuration R, and $R_3$ and $R_4$ each represent a —$OR_6$ group in which $R_6$ is a sodium atom.

7. A pharmaceutical composition including at least one compound according to claim 5, and at least one pharmaceutically acceptable excipient.

8. The method for treatment of an infection caused by an organism that is auxotrophic for purines, said organism being selected from the bacteria and the protozoa, wherein said infection is caused by an agent selected from: *Plasmodium falciparum, Plasmodium vivax, Plasmodium malariae, Plasmodium ovale, Plasmodium knowlesi, Giardia lamblia, Helicobacter pylori, Mycobacterium tuberculosis, Escherichia coli, Trypanosoma brucei, Babesia divergens, Babesia canis* and *Toxoplasma gondii*, and wherein said method comprises administering to a subject in need thereof a pharmaceutical composition according to claim 7.

9. A pharmaceutical composition including at least one compound according to claim 6, and at least one pharmaceutically acceptable excipient.

10. A method for treating malaria caused by *Plasmodium falciparum* infection, the method comprising administering to a subject in need of treatment the composition of claim 7.

11. A pharmaceutical composition including at least one pharmaceutically acceptable excipient, and at least one compound having the following general formula (I):

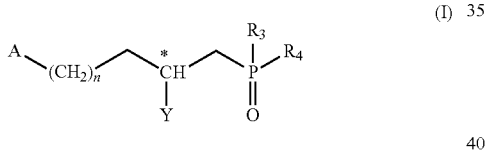

(I)

in which

A represents a heterocycle having formula (IIB) as below:

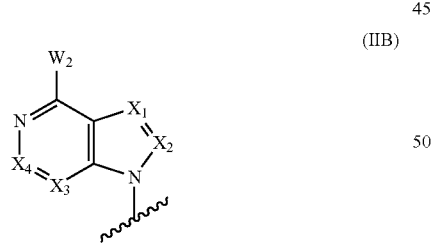

(IIB)

in which:

$W_2$ represents a halogen atom, a —$OR_5$ group, a —$SR_5$ group, a —$NHR_5$ group or a —$N(R_5)_2$ group;

$X_1$ represents a nitrogen atom or a —CH— group;

$X_2$ represents a nitrogen atom, a —$CR_1$ group or a —C═O group;

$X_3$ represents a nitrogen atom or a —CH— group;

$X_4$ represents a nitrogen atom, a —$CR_2$ group or a —C═O group;

$R_1$ represents:
a hydrogen atom, or
a halogen atom, or
a group selected from:
a —$NHR_5$ group,
a —$N(R_5)_2$ group,
a —$OR_5$ group,
a —$SR_5$ group,
a $C_1$-$C_6$ alkyl group,
an aryl group,
a heteroaryl group;

$R_2$ represents:
a hydrogen atom, or
a halogen atom, or
a group selected from:
a —$NHR_5$ group,
a —$N(R_5)_2$ group,
a —$OR_5$ group,
a $C_1$-$C_6$ alkyl group,
an aryl group,
a heteroaryl group;
a $C_2$-$C_6$ alkenyl group,
a $C_2$-$C_6$ alkynyl group,
an aryl ($C_1$-$C_6$)alkyl group,
a ($C_1$-$C_6$)alkylaryl group,
a heteroaryl($C_1$-$C_6$)alkyl group;

$R_3$ and $R_4$, which are identical or different, each represent, independently of one another:
a —$OR_6$ group, or
a —$NHR_7$ group, or
a —$N(R_7)_2$ group;

$R_5$ represents:
a hydrogen atom
a $C_1$-$C_6$ alkyl group,
a $C_2$-$C_6$ alkenyl group,
a $C_2$-$C_6$ alkynyl group,
an aryl group,
a $C_1$-$C_6$ acyl group,
an aryl($C_1$-$C_6$)alkyl group,
said groups optionally containing one or more heteroatoms;

$R_6$ represents:
a hydrogen atom, a sodium atom or a lithium atom, or
a group selected from:
an ammonium group
a —$N(R_aR_bR_cR_d)^+$ group with $R_a$, $R_b$, $R_c$ and $R_d$, which are identical or different, each representing a hydrogen atom or a $C_1$-$C_4$ alkyl group,
an aryl group,
a S—($C_1$-$C_{12}$)alkyl-2-dithioethyl group, said alkyl group optionally including at least one heteroatom,
a S—($C_1$-$C_{12}$)aryl-2-dithioethyl group, said aryl group optionally including at least one heteroatom,
a S—($C_1$-$C_6$)acyl-2-thioethyl group, said acyl group optionally including at least one heteroatom,
a ($C_1$-$C_6$)alkyloxy($C_1C_6$)alkyl ester group,
an alkoxy($C_1$-$C_6$)carbonyloxymethyl ester group,
a $C_{12}$-$C_{20}$ alkyl group optionally including at least one heteroatom, $R_7$ represents:
a $C_1$-$C_6$ alkyl chain,
an aryl group, or
an amino acid residue, an amino acid ester derivative or an amino acid amide derivative;

n is a whole number equal to 0, 1 or 2;

Y represents a substituent selected from: a chlorine atom, bromine atom, iodine atom, a —$OR_5$ group, a —$SR_5$ group, a —$NHR_5$ group and a —$N(R_5)_2$ group;

C* represents a chiral carbon atom, with the exception of the compounds in which:

$W_2$ represents the —$NH_2$ group;

$X_1$ represents a nitrogen atom;

$X_2$ represents a —$CR_1$ group, $R_1$ representing a hydrogen atom;

$X_3$ represents a nitrogen atom;

$X_4$ represents a —$CR_2$ group, $R_2$ representing a hydrogen atom;

n is equal to 1;

Y represents a hydrogen atom, hydroxyl group or an —$NH_2$ group;

the chiral carbon C* has configuration R or S, and $R_3$ and $R_4$ each represent a —$OR_6$ group in which $R_6$ is a sodium atom.

12. A method for treatment of an infection caused by an organism that is auxotrophic for purines, said organism being selected from the bacteria and the protozoa, wherein said infection is caused by an agent selected from: *Plasmodium falciparum, Plasmodium vivax, Plasmodium malariae, Plasmodium ovale, Plasmodium knowlesi, Giardia lamblia, Helicobacter pylori, Mycobacterium tuberculosis, Escherichia coli, Trypanosoma brucei, Babesia divergens, Babesia canis* and *Toxoplasma gondii*, and wherein said method comprises administering to a subject in need thereof a pharmaceutical composition according to claim 11.

13. A method for treating malaria caused by *Plasmodium falciparum* infection, the method comprising administering to a subject in need of treatment the composition of claim 11.

* * * * *